United States Patent [19]

Ko et al.

[11] Patent Number: 5,679,546
[45] Date of Patent: Oct. 21, 1997

[54] CHIMERIC PROTEINS WHICH BLOCK COMPLEMENT ACTIVATION

[75] Inventors: Jone-Long Ko, Sudbury; C. Grace Yeh, Marlborough, both of Mass.

[73] Assignee: Cytomed, Inc., Cambridge, Mass.

[21] Appl. No.: 310,416

[22] Filed: Sep. 22, 1994

Related U.S. Application Data

[63] Continuation-in-part of Ser. No. 126,596, Sep. 24, 1993, abandoned.

[51] Int. Cl.$^6$ .......................... C12N 15/62; C07K 14/705
[52] U.S. Cl. ................... 435/69.2; 435/69.7; 435/240.2; 435/252.3; 435/320.1; 530/350; 530/412; 536/23.4
[58] Field of Search ................................ 530/350, 380, 530/402, 416, 417, 418, 412; 514/2; 435/69.6, 69.7, 240.2, 252.3, 254.2, 320.1, 69.2; 536/23.4

[56] References Cited

U.S. PATENT DOCUMENTS

| 4,774,180 | 9/1988 | Toth et al. | 435/69.7 |
| 5,252,216 | 10/1993 | Folena-Wasserman et al. | 210/635 |
| 5,264,357 | 11/1993 | Caras et al. | 435/240.1 |

FOREIGN PATENT DOCUMENTS

| 0512733 | 11/1992 | European Pat. Off. |
| 9111461 | 8/1991 | WIPO |

OTHER PUBLICATIONS

Lublin et al., "Decay–Accelerating Factor: Biochemistry, Molecular Biology, and Function", Ann. Rev. Immunol., 7:35–58 (1989).

Miyagawa et al., "Effect of Transfectant Molecules, MCP, DAF, and MCP/DAF Hybrid, on Complement Mediated Swine Endothelial Cell Lysis", Molec. Immunol., Abstracts of the XV International Complement Workshop, Kyoto, Japan, 30:(Supp 1), (Sep., 1993).

Lee, et al., "Cloning with Tandem Genes Systems for High Level Gene Expression", 1984, Nucleic Acids Res. 12(17):6797–811.

Telen et al., "Molecular Mapping of the Cromer Blood Group Cr$^a$ and Tc$^a$ Epitopes of Decay Accelerating Factor: Toward the Use of Recombinant Antigens in Immunohematology", Blood, 84(9):3205–11.

Pichler, R., et al., "Tubulointerstitial Disease in Glomerulonephritis: Potential Role of Osteopontin (Uropontin)", 1994, Am. J. Pathology, 144(5):915–23.

Väkevä, A., et al., "Animal Model: Time Course of Complement Activation and Inhibitor Expression after Ischemic Injury of Rat Myocardium", 1994, Am. J. Pathology, 144(6):1357–68.

Adams, E.M., et al., "Contribution of the Repeating Domains of Membrane Cofactor Protein (CD46) of the Complement System to Ligand Binding and Cofactor Activity", 1991, J. Immunol., 147:3005–3011.

Bailey, P.J., et al., "Immune Complexes and Inflammation: A Study of the Activity of Anti–Inflammatory Drugs In The Reverse Passive Arthus Reaction in the Rat", 1983, Biochem. Pharmacol., 32:475–81.

Caldwell, F.T., et al., "Relationships Between Heat Production, Heat Loss, and Body Temperature for Rats With Burn Injuries Between 26% and 63% of the Body Surface Area", 1993, J. Burn Care & Rehab., 14:420–26.

Coyne, K.E., et al., "Mapping of Epitopes, Glycosylation Sites, and Complement Regulatory Domains in Human Decay Accelerating Factor", 1992, J. Immunol., 149:2906–13.

Hosea, S., et al., "Role of Complement Activation in a Model of Adult Respiratory Distress Syndrome", 1980, J. Clin. Invest., 66:375–82.

Hussey, R.E., et al., "A Soluble CD4 Protein Selectively Inhibits HIV Replication and Syncytium Formation", 1988, Nature, 331:78–81.

Iwata, K., et al., "Expression of a Hybrid Complement Regulatory Protein, Membrane Cofactor Protein Decay Accelerating Factor on Chinese Hamster Ovary", 1994, J. Immunol., 152:3436–3444 (Apr. 1, 1994).

Krych, M., et al., "Analysis of the Functional Domains of Complement Receptor Type 1 (C3b–C4b Receptor; CD35) by Substitution Mutagenesis", 1994, J. Biol. Chem., 269:13273–278.

Leventhal, J.R., et al., "Prolongation of Cardiac Xenograft Survival by Depletion of Complement", 1993, Transplantation, 55:857–66.

Linington, C., et al., "The Role of Complement in the Pathogenesis of Experimental Allergic Encephalomyelitis", 1989, Brain, 112:895–911.

Steer, M.L., "Pathobiology of Experimental Acute Pancreatitis", 1992, Yale J. Biol. and Med., 65:421–30.

Weisman, H.F., et al., "Soluble Human Complement Receptor Type 1: In Vivo Inhibitor of Complement Suppressing Post–Ischemic Myocardian Inflammation and Necrosis", 1990, Science, 249:146–51.

Molina et al, "Analysis of Epstein–Barr Virus–binding Sites on Complement Receptor 2 . . .", J. Biol. Chem. 266(19): 12173–12179 (Jul. 1991).

Kalli et al, "Mapping of the C3b–Binding Site of CR1 and Construction of a (CR1)$_2$–F(ab')$_2$ Chimeric . . . ", J. Exp. Med. 174:1451–1460 (Dec. 1991).

Primary Examiner—Stephen Walsh
Assistant Examiner—Karen E. Brown
Attorney, Agent, or Firm—Fish & Richardson P.C.

[57] ABSTRACT

The present invention relates to novel chimeric proteins comprising a first polypeptide which inhibits complement activation, linked to a second polypeptide which inhibits complement activation, nucleic acids encoding novel chimeric proteins and methods of reducing inflammation with the administration of the chimeric proteins of the invention.

14 Claims, 11 Drawing Sheets

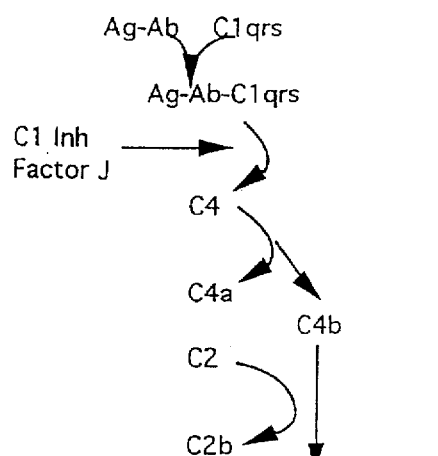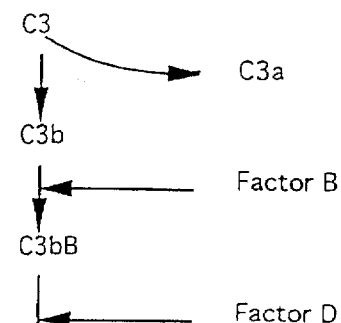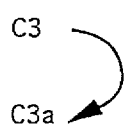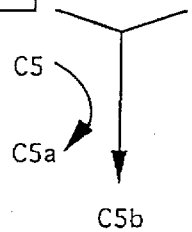
FIG. 1

Microcarrier Produced CAB-2: 7-step Purification contaminant precipitation and removal
media is diluted 1:1,
pH is reduced to 5.0,
precipitate is removed with precipitate-adsorbant (Celite 621)

anion exchange
Q Seph FF - bind at pH 5.0,
wash with 25mM NaCl to remove contaminants,
elute CAB-2 with 200mM NaCl

IMAC
charge resin with $ZnCl_2$,
load at pH 6.0,
collect CAB-2 in flowthough,
elute contaminants with 50mM imidazole

HIC
phenyl 650M HIC - load in 3M NaCl, pH 7.0,
elute CAB-2 with 1M NaCl

HIC
butyl 650M HIC - load in 3M NaCl, pH 7.0,
elute CAB-2 with 1M NaCl

diafiltration/concentration
diafilter the pool into PBS,
CAB-2 concentrated to 15-20 mg/ml

endotoxin removal/final concentration
pool is passed over detoxigel column twice,
CAB-2 concentrated to >10 mg/ml

FIG. 6

CHIMERIC PROTEINS WHICH BLOCK COMPLEMENT ACTIVATION

This application is a continuation-in-part of U.S. Ser. No. 08/126,596, filed Sep. 24, 1993, now abandoned.

FIELD OF THE INVENTION

This invention relates to complement inhibition and inflammation.

BACKGROUND OF THE INVENTION

The complement system includes a group of proteins in blood plasma which plays an integral role in immune and allergic reactions. Activation of complement can occur via at least two pathways: the classical pathway involving antigen-antibody complexes, and the alternative pathway involving cell wall polysaccharides of yeast and bacterial microorganisms. Regardless of which initiation pathway is used, the end result is the formation of activated fragments of complement proteins (e.g. C3a, C4a, and C5a anaphylatoxins and C5b-9 membrane attack complexes) which mediate several functions including leukocyte chemotaxis, activation of macrophages, vascular permeability and cellular lysis (Frank, M. and Fries, L. Complement. In Paul, W. (ed.) *Fundamental Immunology*, Raven Press, 1989).

Several regulatory proteins of the complement system have been identified (FIG. 1). Their primary functions are to regulate the activity of C3/C5 convertases for prevention of excessive complement activation and autolytic destruction of host tissues. These complement regulators are either soluble plasma proteins or integral membrane proteins expressed on a variety of cell types. The former include C4b binding protein (C4bp) and Factor H. The latter include the C3b/C4b receptor (Complement receptor 1, CR1, CD35), membrane cofactor protein (MCP, CD46), and decay accelerating factor (DAF, CD55). These proteins possess many structural similarities. Each is composed of multiple short consensus repeats (SCRs) of approximately 60 amino acids in length having conserved cysteine, glycine and proline residues. The genes encoding these proteins have been localized to chromosome 1 and are collectively known as the regulators of complement activation (RCA) gene cluster (Hourcade, D. et al, 1989, Adv. Immunol. 45:381). In addition to its role in regulating complement activation, erythrocyte CR1 also functions as a receptor for circulating immune complexes to promote their clearance from plasma (Cornacoff, J. et al, 1983, J. Clin. Invest. 71:236).

MCP and DAF are important regulatory proteins of the complement system which function to prevent autolytic destruction of host tissues by complement activation.

MCP was initially purified and characterized by Seya and coworkers (J. Exp. Med. 1986, 163:837; Biochem. J., 1989, 264:581), who showed that it binds C3b and C4b and possesses Factor I cofactor activity. MCP therefore functions to irreversibly inactivate C3b and C4b by proteolytic cleavage to C3bi and C4bi (see FIG. 2). MCP has been shown to bind preferentially to C3b, thus making it a more potent inactivator of alternative pathway convertases (Seya, T. et al, 1991, Mol. Immunol. 28:1137).

DAF was first identified by Nicholson-Weller and coworkers (J. Immunol., 1982, 129:184) and characterized by Medof and coworkers (J. Exp. Med., 1984, 160:1558). DAF also binds to C3b and C4b and functions to dissociate these molecules from the C3 convertase, thus promoting the decay (inactivation) of the convertase (see FIG. 3). DAF similarly inactivates both alternative and classical convertases.

MCP and DAF are composed of only four SCRs, making them the smallest of the complement regulatory proteins. MCP does not possess decay accelerating activity and DAF does not possess cofactor activity. Both proteins are expressed in a variety of cell types, including endothelial cells, fibroblasts, lymphocytes, granulocytes and monocytes (Hourcade,D. et al, 1989, Adv. Immunol. 45:381; McNearny,T. et al, 1989, J. Clin. Invest. 84:538). MCP and DAF are considered to function, via different complementary mechanisms, as intrinsic inhibitors of complement activation to prevent complement-mediated autolysis of host cells.

SUMMARY OF THE INVENTION

The invention features a chimeric protein in which a first polypeptide which inhibits complement activation is linked to a second polypeptide which inhibits complement activation. The chimeric protein is preferably a soluble protein. The first and second polypeptides of the chimera may be the same or different, and the first polypeptide may be linked to the second polypeptide by a peptide bond.

In a preferred embodiment, the first polypeptide is MCP or a soluble, biologically active fragment thereof, e.g., a fragment containing at least regions 2, 3, and 4 of the SCR of MCP, and the second polypeptide is DAF or a soluble, biologically active fragment thereof, e.g., a fragment containing at least regions 2, 3, and 4 of the SCR of DAF. As used herein, the term "fragment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and most preferably at least about 60 to 80 or more contiguous amino acids in length. Such polypeptides can be generated by methods known to those skilled in the art, including proteolytic cleavage of the protein, de novo synthesis of the fragment, or genetic engineering. A biologically active fragment is defined as one which exhibits complement inhibitory activity. The activity of a fragment should be at least 1% of, is more preferably at least 10% of, yet more preferably at least 50% of, and is most preferably at least equal to, the biologically activity of the naturally occurring inhibitor of complement activation.

The soluble chimeric molecules are more effective inhibitors of complement activation than the soluble MCP or DAF proteins, individually or in combination. Furthermore, the soluble chimeric proteins possess extrinsic complement regulatory activity (the ability to inactivate convertases not bound to the same cell membrane). In contrast, the membrane-associated forms of MCP and DAF possess intrinsic activity (the ability to inactivate convertases bound only to the same cell membrane). The chimeric proteins can be used as a therapeutic treatment for inflammatory and autoimmune diseases, and monoclonal antibodies produced against the chimeric proteins can be used as diagnostic or therapeutic agents.

The invention also includes modifications of the chimeric proteins of the invention. Modifications (which do not normally alter primary sequence) include in vivo, or in vitro chemical derivatization of polypeptides, e.g., acetylation, or carboxylation. Also included are modifications of glycosylation, e.g, changing glycosylation patterns, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

In another embodiment, the first and second polypeptides of the chimera may be selected from the group consisting of MCP, DAF, complement receptor 1, factor H, C4b binding protein, and soluble biologically active fragments thereof. Because of their C3/C5 convertase-inhibiting activities, any of the complement regulatory proteins or polypeptides of the RCA family could be the first or second polypeptide of the chimera.

The invention also includes a nucleic acid sequence encoding the chimeric protein in which the first and second polypeptides are linked by a peptide bond and a recombinant expression vector comprising a selectable marker, e.g., glutamine synthetase or dihydrofolate reductase, and a nucleic acid encoding the chimeric protein of the invention operably linked to regulatory sequences for expression of said protein, e.g., a mammalian promoter. The invention also includes a process for preparing the chimeric proteins of the invention by culturing the chimeric protein-encoding expression vector in suitable host cells, e.g., bacterial cells, yeast cells, insect cells, or mammalian cells, under conditions which promote expression of the chimeric protein. The process is preferably carried out by expressing the chimeric protein in Chinese hamster ovary (CHO) cells. The chimeric protein may be prepared by collecting a cell culture supernatant or cell lysate of the host cells; removing acid-precipitable contaminants e.g., contaminants which precipitate below pH 7.0, e.g., contaminants which precipitate upon diluting the supernatant or lysate 1:1 with 25 mM piperazine at a pH 5.0, from the supernatant or lysate; collecting the chimeric protein which binds to an anion exchange resin; removing metal-binding contaminants; binding the chimeric protein to a phenyl hydrophobic interaction resin and then eluting said recombinant protein; binding the chimeric protein to a butyl hydrophobic interaction resin and then eluting said recombinant protein; and removing endotoxin from the chimeric protein. The last three steps of the inventive process may be carried out in any order.

The invention also includes a method of inhibiting C3a and C5a generation by contacting a C3 convertase, e.g., the C3b and C4b subunits of the C3 convertase, and a C5 convertase, e.g., the C3b and C4b subunits of the C5 convertase, with the chimeric protein of the invention. The binding of the chimeric protein of the invention to the convertases inhibits the enzymatic activity of the convertases, thus inhibiting the generation of C3a and C5a.

In another aspect, the invention features a method of reducing inflammation characterized by excessive complement activation by administering the chimeric protein of the invention to a patient afflicted with such a condition.

In a final aspect, the invention features an antibody which binds to the chimeric protein of the invention, but does not bind to the first polypeptide or second polypeptide of the chimera alone.

Other features and advantages of the invention will be apparent from the following detailed description and from the claims.

DETAILED DESCRIPTION

The drawings will first be briefly described.

FIG. 1 is a diagram showing the proteins of the complement system, their pathways of activation, and the proteins regulating their function.

FIG. 2 is a diagram showing the mechanism of C3 convertase inactivation by MCP.

FIG. 3 is a diagram showing the mechanism of C3 convertase inactivation by DAF.

FIG. 4 is a graph showing the time course of cell density and supernatant concentration of complement activation blocker-2 (CAB-2) protein in a 12-liter microcarrier culture of transfected CHO-K1 cells. Culture vessels were seeded with transfected cells at $8\times10^4$ cells/ml in Iscove's modified Dulbecco's medium (IMDM) containing 2.5 g/ml microcarriers and 10% fetal bovine serum. After several days of growth to reach peak cell density, the culture medium was switched to serum-free IMDM. Every day thereafter, 10 liters of culture supernatant was harvested and replaced with fresh serum-free medium.

FIG. 5 is a photograph of purified soluble MCP (sMCP) and CAB-2 proteins separated on a polyacrylamide gel. Five µg aliquots of each purified protein was electrophoresed on a 10% polyacrylamide sodium dodecyl sulfate (SDS) gel. The gel was run under reducing conditions and stained with Coomassie blue. Lane 1, molecular weight markers; Lane 2, sMCP; Lane 3, CAB-2. The molecular weight standards are 106, 80, 49.5, 32.5 and 27.5 kDa.

FIG. 6 is a diagram depicting the seven-step purification process for microcarrier-produced CAB-2 protein.

FIG. 7 is a line graph showing the dual reactivity of CAB-2 protein with anti-MCP and anti-DAF antibodies as measured in an enzyme-linked immunosorbent assay (ELISA). The assay used a rabbit anti-MCP polyclonal antibody capture, murine anti-DAF monoclonal secondary, and horseradish peroxidase (HRPO)-conjugated goat anti-mouse IgG tertiary antibodies.

FIG. 8 is a line graph showing a comparison of sMCP and CAB-2 activity as measured in a cofactor assay. Cleavage of the potassium bromide-treated C3 with C3b-like properties (iC3) alpha chain was quantitated by scanning densitometry based on the relative proportions of the intact chain and its cleavage products in each sample.

FIG. 9 is a line graph showing a comparison of sDAF and CAB-2 activity as measured in a decay accelerating factor assay. The Z values (number of lytic sites/cell) were determined, using a standard table, from the values of percentage maximum lysis of each sample.

FIG. 10 is a line graph showing a comparison of the inhibitory activities of sMCP, sDAF, a mixture of sMCP+sDAF, and CAB-2 in an assay of classical pathway dependent complement-mediated cell lysis. IgM-sensitized sheep red blood cells (RBC) were the stimulant and human serum (1:200 final dilution) was used as the complement source.

FIG. 11 is a line graph showing a comparison of the inhibitory activities of sMCP and CAB-2 in an assay of alternative pathway dependent complement-mediated cell lysis. Unsensitized guinea pig RBC in a buffer containing EGTA (to chelate $Ca^{+2}$) were the stimulant and human serum (1:4 final dilution) was the source of complement.

FIG. 12 is a line graph showing the inhibition of C5a production by sMCP and CAB-2. Human serum diluted 1:8 was the source of complement and zymosan (1 mg/ml final concentration) was the stimulant for alternative pathway activation. C5a was quantitated by competitive radioimmunoassay with $^{125}$I-C5a desArg.

FIG. 13 is a line graph showing the pharmacokinetics of sMCP and CAB-2 in rats. Animals were injected intravenously with 1 mg/kg dose of purified protein and blood samples drawn at the indicated times post-injection. Plasma levels of sMCP and CAB-2 were determined by ELISA.

FIG. 14 is an autoradiograph of serum samples recovered from rats injected intravenously (i.v.) with $^{125}$I-labeled CAB-2. Serum samples were obtained from rats at various times after injection and electrophoresed on a 10% polyacrylamide SDS gel. The gel was dried and autoradiographed.

FIG. 15 is a bar graph showing the in vivo inhibition of the reversed passive Arthus reaction in guinea pigs by CAB-2 protein. Animals were injected i.v. with 20 mg/kg ovalbumin and 1 μCi $^{125}$I-BSA, then challenged intradermally (i.d.) with 10 mg anti-ovalbumin polyclonal antibody containing the indicated amounts of CAB-2 protein. After 3 h, animals were sacrificed and skin biopsies counted to quantitate leakage of $^{125}$I-BSA.

DETAILED DESCRIPTION

Figure 2:
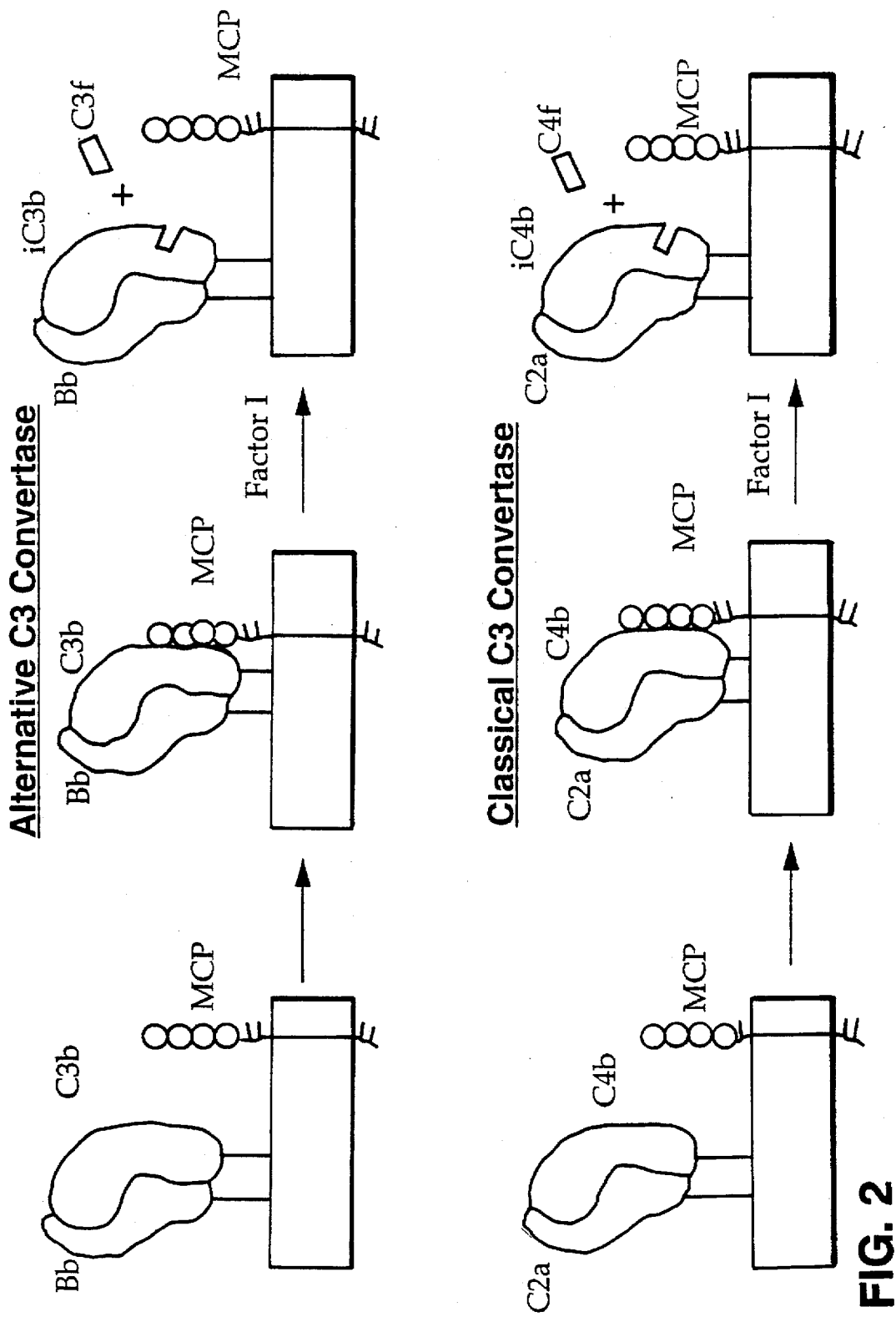
Figure 3:
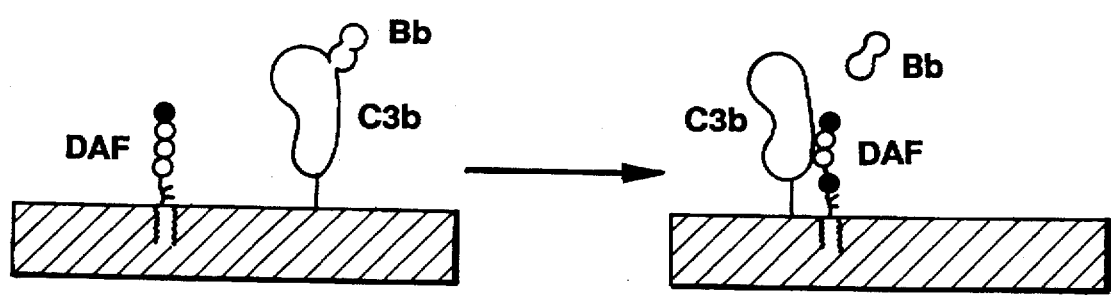

Described herein are the generation and use of novel chimeric genes and their encoded proteins which express the biological activities of both MCP and DAF. The term Complement Activation Blocker (CAB) is defined as a recombinant chimeric protein possessing two different complement inhibiting activities, such as Factor I cofactor activity and decay accelerating activity.

The genes of the invention are constructed in a manner such that the encoded proteins possess at least two complement binding sites and both Factor I cofactor activity and decay accelerating activity.

The chimeric molecules are more effective inhibitors of complement activation than the MCP or DAF proteins, individually or in combination. The chimeric proteins can be used to treat inflammatory and autoimmune diseases, and monoclonal antibodies produced against the chimeric proteins can be used as diagnostic or therapeutic agents.

The invention includes recombinant genes which encode chimeric proteins which have both the Factor I cofactor and the decay accelerating factor regulatory activities for complement. By exhibiting both biological activities, the chimeric proteins are more potent in their abilities to inhibit complement activation than either membrane cofactor protein, decay accelerating factor, or both proteins in combination. Recombinant materials and methods used to construct and express the genes, methods used for its manufacture in useful quantities, pharmaceutical compositions containing the chimeric recombinant proteins, methods for their use in the treatment of inflammatory and autoimmune diseases are described below. Monoclonal antibodies raised against the chimeric complement regulatory proteins, and methods for their production and characterization are also described. Such monoclonal antibodies are useful as reagents for quantitation and monitoring of the chimeric proteins and as diagnostic and therapeutic agents for human diseases.

Specific embodiments of the invention are described in the examples below which detail the construction, cloning and production of a specific chimeric protein, CAB-2. In addition, the examples detail assays which measure the in vitro biological activity of the CAB-2 protein, e.g., the enhanced inhibitory potency for classical and alternative complement activation of CAB-2. Further, the examples describe the in vivo pharmacokinetic behavior of the CAB-2 protein and its efficacy as a treatment for complement-induced inflammation in an animal model.

Cloning and expression of a complement receptor fusion protein with membrane cofactor and decay accelerating activities cDNA clones encoding MCP and DAF proteins, described by Lublin, D. M. et al., 1989, J. Exp. Med. 168:181–194, and Medof, M. E. et al., 1987, Proc. Natl. Acad. Sci. USA 84:2007–2011, both of which are herein incorporated by reference, were used for the construction of expression vectors that direct the synthesis of MCP and DAF fusion proteins. The MCP and DAF proteins and/or their biologically active fragments or derivatives may be produced using known recombinant DNA techniques based on the cDNA sequences published by Lublin D. M. et al, supra and Medof, D. E., et al., supra. Specifically, mRNA can be isolated from cells expressing MCP and DAF, cDNA synthesized using random primers, and the specific sequence for the corresponding gene amplified by polymerase chain reaction (PCR) with a pair of primers synthesized according to the published sequences. cDNA encoding other proteins which inhibit complement activations can also be isolated in the similar fashion, e.g., C4b-binding protein (Chung et al., 1985, Biochem J. 230:133–141, herein incorporated by reference), e.g., factor H (Ripoche et al., 1988, Biochem. J. 249:593–602, and EMBL Accession Number Y00716, herein incorporated by reference), e.g., CR1 (Klickstein et al., 1988, J. Exp. Med. 168:1699, herein incorporated by reference).

The short consensus repeats (SCR) region 3 and 4 confer the C3b and C4b binding sites of MCP protein (Adams, et al., 1991, J. Immunol. 147:3005–3011). However, SCR 2 is also required in addition to SCR 3 and 4 to retain the membrane cofactor activity. The minimal length of cDNA to be used is that which encodes the amino acids corresponding to both SCR 3 and 4 of MCP. The SCR 2, 3 and 4 of DAF contribute to the decay accelerating activity (Coyne, et al., 1992, J. Immunol. 149:2906–2913). For example, a cDNA segment encoding the extracellular domain containing SCR1–4 and/or serine-threonine-proline rich (ST) regions of MCP and DAF proteins can be used for the production of the fusion protein. Genes other than MCP and DAF with C3b and C4b binding activities and membrane cofactor and/or decay accelerating activity can also be used for the construction of expression vectors that direct the synthesis of fusion proteins with membrane cofactor and decay accelerating activities.

Linker between both genes in an expression vector

A linker segment of DNA can be added between two genes during the construction of expression vectors. However, insertion of a linker segment between the coding regions of the first and second proteins must maintain a proper reading frame at the 5' and 3' ends to insure continuous protein translation.

The length of the linker can range from 0 to 1500 amino acids long and is preferably 0-60 amino acids long. As described below, no amino acids have been added at the junction for MCP-DAF construct but two newly added amino acids have been added at the junction for MCP-MCP, MCP-1/2MCP and DAF-MCP constructs. Since deletion of SCR 1 region does not impair the cofactor activity of MCP, the SCR 1 region in DAF-MCP construct which spans about 60 amino acids long, can be considered part of a linker in addition to the two newly added amino acids.

Amino acid substitutions: manipulating the C3b and C4b binding specificities and affinities All the SCR regions in the family of complement regulatory genes share a unique feature of a consensus sequence in which all four cysteines form two disulfide bonds within the region. Amino acids can be substituted from one SCR to another to convert the binding specificity of one SCR or to increase binding affinity to another. For example, C3b binding can be converted to C4b binding or to both specificities in CR1 (Krych et al., 1994, J. Biol. Chem. 269:13273–13278). These manipulations can be accomplished using site directed mutagenesis techniques known in the art.

Genes to be used for the construction of fusion proteins

All members of the regulators of complement gene cluster RCA share basic structural similarity (Hourcade, Holers and Atkinson, 1989, Adv. Immunol. 45:381–416). Specifically, they are composed of several SCRs of about 60 amino acids long with four conserved cysteines. All except MCP and DAF contain more than 4 SCR regions. For example, CR1 has 30 SCR regions. Fusion proteins retaining membrane cofactor activity and decay accelerating activity can be constructed with more than two genes, each with membrane cofactor or decay accelerating activity. The length for each cDNA segment to be used in the construct is discussed above.

Post-translational modification of fusion proteins

Fusion proteins can be produced with or without glycosylation. Most members of the RCA family have sites for glycosylation. For example, MCP contains three N-linked and one O-linked glycosylation sites within the SCR and ST regions, respectively. DAF contains one N-linked and multiple O-linked oligosaccharides (Lublin, et al., 1986, J. Immunol. 137:1629). In general, production of the protein in an eucaryotic expression system results in the expression of the corresponding protein in glycosylated form. There are three possible ways to produce non-glycosylated fusion proteins: (1) deglycosylation by cleavage of carbohydrate groups enzymes such as Endo-peptide-N-galactosaminidase and O-glycanase to cleave N- and O-linked glycosylations, respectively; (2) procaryotic expression in bacillus and *E. Coli* to generate non-glycosylated fusion proteins; (3) site-directed mutagenesis to alter the recognition sites for N- or O-linked glycosylation.

Expression systems

Fusion proteins can be produced in procaryotic and eucaryotic systems each using different expression vectors that are appropriate for each host system.

Chimeric proteins of the invention can be produced in an eucaryotic expression system such as the baculoviral or mammalian systems described below.

The following are examples of expression vectors which may be used for gene expression in an eucaryotic expression system. The plasmid, pMSG, uses the promoter from mouse mammary tumor virus long terminal repeat (MMTV). Suitable host cells for pMSG expression are chinese hamster ovary (CHO) cells, HeLa cells and mouse Lkt negative cells (Lee, F., et al., 1981 Nature 294:228–232). The vector, pSVL, uses the SV40 late promoter. For high transient expression, suitable host cells for pSVL expression are Cos cells (Sprague, J. et al., 1983, J. Virol. 45:773–781). The vector, pRSV, uses Rous Sarcoma Virus promoter. Suitable host cells RSV expression are mouse fibroblast cells, lymphoblastoid cells and COS cells (Gorman, Padmanabhan and Howard, 1983, Science 221:551–553).

Baculovirus expression vectors can also be used. These vectors are stably expressed in insect cells such as sf9 (Luckow, V. A. and Summers, M.D., 1988, Bio/Technology 6:47–55; Miller, L. K., 1988, Ann. Re. Microbiology 42:177–199).

Chimeric proteins of the invention can also be produced in a procaryotic expression system. The following are examples of expression vectors which can be expressed in procaryotic expression systems.

The pOX expression series using the oxygen-dependent promoter can be expressed in *E. coli*. (Khosla, G., et al., 1990, Bio/Technology 8:554–558). pRL vector which uses the strong pL promoter of lambda phage (Reed, R. R., 1981, Cell 25:713–719; Mott, J. D., et al., 1985, Proc. Natl. Acad. Sci. USA 82:88–92) and the pKK223-3 vector which uses a hybrid promoter derived from the fusion between the promoters of the tryptophan and lactose operons of *E. coli*. (Borsius, J. and Holy, A., 1984, Proc. Natl. Acad. Sci. USA 81:6929–6933) can be used for expression in *E. coli*.

Suitable vectors for yeast expression are also well known in the art, e.g. Sleep, D. Belfield, D. P. and Goodey, A. R., 1990, Bio/Technology 8:42–46; Sakai, A. et al., 1991, Bio/Technology 9:1382–1385; Kotula, L. and Curtis, P. J., 1991, Bio/Technology 9:1386–1389 all of which are herein incorporated by reference.

Production, quantitation, purification and analysis of chimeric CABs

Once a recombinant cell line that expresses a chimeric gene has been isolated, the secreted proteins must be identified and verified with regard to their predicted structure. Various methods can be used to identify and characterize the expressed chimeric proteins. The recombinant cell line can first be incubated with $^{35}$S-methionine to endogenously label its expressed proteins. The presence of secreted chimeric proteins can be verified by radioimmunoprecipitation with monoclonal antibodies to one or the other protein of the chimera, e.g., anti-MCP or anti-DAF. Antibodies to both MCP and DAF are commercially available.

In an example of one method, metabolically $^{35}$S-labeled culture supernatants are incubated with either anti-MCP or anti-DAF monoclonal antibodies. The immune complexes are precipitated by incubation with Protein A conjugated to Sepharose. SDS polyacrylamide gel electrophoresis of the immunoprecipitated proteins, followed by autoradiography, can be used to identify the secreted chimeric proteins. If a chimeric protein is expected to express both MCP and DAF domains, as is the case with CAB-2, one would expect both anti-DAF and anti-MCP antibodies to immunoprecipitate the protein.

Another method that could be used with bispecific chimeric proteins composed of both MCP and DAF gene segments (e.g., CAB-2) is a double immunoprecipitation, using two monoclonal antibodies of different specificities in succession. Pre-clearance of culture supernatant with one antibody would result in a negative immunoprecipitation with the second antibody. This method would verify that a single protein expresses both MCP and DAF epitopes.

Alternatively, a bispecific chimeric protein, e.g, CAB-2, can be identified by Western blot. For example, after SDS-PAGE and transfer to nitrocellulose, blots can be developed with either anti-MCP or anti-DAF monoclonal antibodies. The expressed bispecific recombinant protein would be reactive with both antibodies, again demonstrating the presence of both MCP and DAF epitopes on the chimera.

Identification of a bispecific chimeric protein such as CAB-2 can also be accomplished by ELISA. For example, a rabbit polyclonal antibody specific for either MCP or DAF can be used to coat plastic microtiter ELISA plates, followed by the addition of culture supernatant from the recombinant cell line expressing CAB-2 and incubation with the capture polyclonal antibody. A monoclonal anti-DAF or anti-MCP secondary antibody, the specificity of which is different from the capture antibody, can be subsequently used. A positive reaction would indicate the presence of both epitopes on the chimeric protein.

An ELISA can also be used to quantitate the levels of CAB-2 in culture supernatants or any other unpurified solutions containing the chimeric protein by comparison to standard curve of known quantities of purified CAB-2 protein. Quantitation of CAB-2 would be useful for determination of production rates in recombinant cell lines, determination of protein concentration in partially purified preparations, and for determination of protein concentration in plasma for in vivo experiments.

The chimeric CAB-2 protein can be purified from recombinant cell culture supernatant by a variety of standard chromatographic procedures, including but not limited to immunoaffinity chromatography, ion exchange chromatography, gel filtration chromatography, reverse-phase high pressure liquid chromatography (HPLC), lectin affinity chromatography, or chromatofocusing. For example, small quantities of culture supernatant containing serum supplement can be purified using immunoaffinity chromatography with e.g., anti-MCP or anti-DAF monoclonal antibodies. CAB-2 protein bound to the immobilized antibody can be eluted in purified form by use of a chaotropic solution.

Recombinant CHO cells can be cultured without high concentrations of serum supplement for production of large quantities (100 liters) of supernatant containing CAB-2 protein. A description of a culture method which uses microcarriers in 12-liter vessels is presented in an example below. The CAB-2 protein in this serum-free culture supernatant can be purified by the chromatographic procedures detailed in the example below. This procedure results in hundreds of mg of CAB-2 protein which is greater than 90% pure.

Once the CAB-2 protein is purified, its amino acid sequence can be deduced by direct protein sequence analysis using an automated system. The presence of N- and O-linked carbohydrates can be determined by use of specific endoglycosidase enzymes (Chavira, R. et al, 1984, Anal. Biochem. 136:446). Further characterizations of its biochemical structure can also be performed, including but not limited to pI determination by isoelectric focusing, hydrophilicity analysis, X-ray crystallographic analysis, and computer modeling.

Functional characterization of the chimeric proteins of the invention

The important characteristic for the chimeric recombinant proteins is their ability to function both as a cofactor for Factor I and as a decay accelerating factor. In vitro assays can be performed to measure these biological activities (Medof, M. et al, 1984, J. Exp. Med. 160:1558; Masaki, T. et al, 1992, J. Biochem 111:573). As described in the examples, assays for cofactor activity (using purified C3 and factor I) and for decay accelerating activity (using IgM, C1 and C4-sensitized sheep RBC and purified C2) are used to demonstrate both these complement regulatory functions for the CAB-2 chimeric protein. The consequence of either cofactor or decay accelerating activity, or in the case of CAB-2, both activities in combination, is the inactivation of C3/C5 convertases. Another in vitro assay, as described in the examples below, demonstrates that CAB-2 is capable of inhibiting C5 convertase activity as measured by the production of C5a (Moran, P. et al, 1992, J. Immunol. 149:1736, herein incorporated by reference). Additional assays, as described in the examples below, demonstrate that CAB-2 inhibits the complement-induced lysis of cells via the classical and alternative pathways.

Generation of Monoclonal Antibodies Against Chimeric Proteins

Monoclonal antibodies can be generated to purified chimeric proteins by standard procedures. Mice are immunized with the proteins mixed with a suitable adjuvant. Spleen cells are fused with a myeloma cell line using polyethylene glycol, and the hybridomas are selected with medium containing hypoxanthine and aminopterin. Hybridomas secreting the desired antibodies can be screened by ELISA and cloned. Specificities of the monoclonal antibodies can be determined by the use of different protein or peptide antigens in the ELISA. Useful quantities of antibodies can be produced by either the generation of ascites fluid in mice or by large scale in vitro culture of the cloned antibody-producing hybridoma cell line. Antibodies can be purified by various chromatographic procedures known in the art, such as affinity chromatography on either immobilized Protein A or Protein G.

Demonstration of in vivo Therapeutic Activity of CAB-2

The Arthus reaction is an inflammatory response caused by the interaction of antigen in tissue with circulating antibody. It has been used as a classic example of a localized in vivo inflammatory response, and is characterized by the formation of immune complexes, complement activation, inflammatory cell recruitment, edema and tissue damage (P. Bailey & A. Sturm, 1983, Biochem. Pharm 32:475). Experimentally, a reversed passive Arthus reaction can be established in an animal model by i.v. injection with antigen and subsequent challenge with antibody. Using guinea pigs as an animal model, the in vivo therapeutic efficacy of chimeric proteins of the invention can be evaluated (see example below).

Additional animal models with relevance to various clinical human diseases can also be used to test the in vivo efficacy of complement activation blockers. These include, but are not limited to: myocardial ischemia/reperfusion injury (acute myocardial infarction; H. F. Weisman et al., 1990, Science 249:146); cerebral ischemic injury (stroke; L. Chang et al, 1992, J. Cerebr. Blood Flow Metab. 12:1030); lung injury (ARDS; S. Hosea et al, 1980, J. Clin. Invest. 66:375); xenograft rejection (transplants; J. Leventhal et al, 1993, Transplantation 55:857); burn injury (F. Caldwell et al, 1993, J. Burn Care Rehab. 14:420); acute pancreatitis (M. Steer, 1992, Yale J. Biol. Med. 65:421), nephritis (R. Pichler et al, 1994, Am. J. Pathol 144:915), cardiopulmonary bypass (L. Nilsson et al., 1990, Artif. Organs 14:46), and multiple sclerosis (C. Linington et al., 1989, Brain 112:895).

Use

The chimeric proteins of the invention, e.g., recombinant CAB-2 protein, can be combined with an appropriate pharmaceutical formulation and administered by a variety of routes, including, but not limited to, intravenous bolus injection, intravenous infusion, intraperitoneal, intradermal, intramuscular, subcutaneous, intranasal, and oral routes. The administration of CAB-2 in vivo will enable the protein to bind endogenous C3/C5 convertases and inhibit the generation of additional C3b and C5b, of C3a and C5a anaphylatoxins, and of C5b-9 lytic complexes. The complement regulatory activities of the CAB-2 protein can therefore function to inhibit in vivo complement activation and the inflammatory sequelae that accompany it, such as neutrophil recruitment and activation, autolysis of host cells, and edema. CAB-2 can be used for the therapy of diseases or conditions that are mediated by inordinate and/or excessive activation of the complement system. These include, but are not limited to: tissue damage due to ischemia-reperfusion following myocardial infarction, aneurysm, stroke, hemorrhagic shock, or crush injury; burns; endotoxemia and septic shock; adult respiratory distress syndrome (ARDS); hyperacute rejection of grafts; cardiopulmonary bypass and pancreatitis. Autoimmune disorders including, but not limited to, systemic lupus erythematosis, rheumatoid arthritis, and multiple sclerosis, can also be treated with the chimeric proteins of the invention (also see Table 1).

TABLE 1

Potential Clinical Targets of Protein Chimeras of the Invention

| Alternative Pathway | Classical Pathway |
| --- | --- |
| Reperfusion injury | Autoimmune diseases |
| Cerebral infarction (stroke) | Systemic lupus erythematosus |
| Acute myocardial infarction | Rheuinatoid arthritis |
| Hypovolemic shock | Glomerulonephritis |
| Multiple organ failure | Hemolytic anemia |
| Crush injury | Myasthenia gravis |
| Intestinal ischemia | Multiple sclerosis |
|  | Vasculitis |
|  | Inflammatory bowel diseases |
|  | Bullous diseases |
|  | urticaria |
|  | Paroxysmal nocturnal hemoglobinuria |
|  | Cryoglobulinemia |
| Inflammatory disorders | Inflammatory disorders |
| Adult respiratory distress syndrome | Septic shock & endotoxemia |
| Thermal injury (burn & frostbite) |  |
| Post-pump syndrome (cardiopulmonary bypass & hemodialysis) |  |
| Crohn's disease |  |
| Sickle cell anemia |  |
| pancreatitis |  |
| Adverse drug reactions | Transplant rejection |
| Drug allergy | Hyperacute allograft |
| Radiographic contrast media allergy |  |
| IL-2 induced vascular leakage syndrome |  |
| Transplant rejection |  |
| Hyperacute xenograft |  |

Various delivery systems are known and can be used to deliver the chimeric proteins of the invention, such as encapsulation in liposomes, or controlled release devices. The chimeric proteins of the invention can also be administered extracorporeally, e.g., pre-conditioning donor organs prior to transplantation. The chimeric proteins of the invention can be formulated in a pharmaceutical excipient in the range of approximately 10 μg/kg and 10 mg/kg body weight for in vivo or ex vivo treatment.

The following examples contained herein are intended to describe but not limit the invention.

EXAMPLE 1

Cloning and expression of a recombinant gene encoding a complement receptor fusion protein Described herein is the construction of various expression vectors that directed the expression of complement receptor fusion proteins, e.g., MCP-MCP, MCP-1/2MCP, MCP-DAF and DAF-MCP. These proteins were prepared as follows. A DNA fragment encoding an amino acid sequence corresponding to the extracellular domains of MCP and DAF were joined together in an expression vector that directed the expression of the fusion MCP and DAF.

All restriction endonucleases were purchased from New England Biolabs, Beverly, Mass. Taq polymerase was obtained from Cetus, Norwalk, Conn. Custom synthesized oligo-nucleotides were purchased from National Biosciences Inc., Plymouth, Minn. pGEM-3fz(−) plasmid (referred to herein as pG3N) was obtained from Promega, Madison, Wis. pBluescript II SK(+) (referred to herein as pII SK) was procured from Stratagene, La Jolla, Calif.

COS-7 (ATCC No. CRL1651) was routinely maintained in Dulbecco's modified Eagle medium (DMEM) (GIBCO) supplemented with 10 mM glutamine, 20 mM HEPES, 50 μg/ml streptomycin,, 50 units/ml penicillin, and 10% fetal bovine serum. CHO-K1 (ATCC No. CCL61) was cultured in Ham's nutrient mixture F-12 (Sigma, St. Louis, Mo.) containing 10% fetal bovine serum, 50 μg/ml streptomycin and 50 units/ml penicillin.

A. Construction of MCP-pG3N plasmid.

MCP-pG3N was used as the backbone for the construction of MCP-DAF, MCP-MCP and MCP-1/2MCP expression vectors. The construction of the MCP-pG3N plasmid was accomplished by the insertion of a cDNA segment encoding an amino acid sequence corresponding to the extracellular domain of MCP into the pG3N plasmid. The cDNA encoding the extracellular domain of MCP was obtained by PCR.

The PCR reaction was carried out under conditions described in S. J. Scharf. 1990, PCR protocol: A guide to methods and applications, ed. M. A. Innis, D. H. Gelfrand, J. J. Sninsky and J. J. White, New York, N.Y., pp. 84–91; herein incorporated by reference. In a typical 100 μl reaction, the reaction mixture contained 50 mM KCl, 10 mM Tris-HCl pH 8.3, 1.5 mM $MgCl_2$, 0.2 mM of all four deoxyribonucleotides, 1 ng of linearized template, 45 pmole of each of the paired primers, and 5 units of Taq polymerase. The amplification reaction was run for 30 cycles with each cycle consisting of an incubation at 94° C. for 1 minute, 52° C. for 1 minute and 72° C. for 1 minute. At the end of the last cycle, a further incubation at 72° C. for an additional 15 minutes was allowed in order to complete the amplification reaction.

A plasmid containing cDNA sequence encoding amino acid sequence corresponding to the MCP protein (Lublin et al., 1988, J. Exp. Med. 168:181–94, herein incorporated by reference) was used as template in the PCR reaction described below.

In the PCR, MCP-N1 primer, 5'—GGA ATT CGC ATG GAG CCT CCC GGC—3'(SEQUENCE ID NO:1) was used as the forward primer, while MCP-STB primer, 5'—CTA TGA GGC ACT GGA CGC TGG AGA TTT—3' (SEQUENCE ID NO:2), was used as the reverse primer. There was an EcoRI restriction site added to the 5' end of the MCP-N1 primer and a termination codon added to the 5' end of the MCP-STB primer for the termination of protein translation.

MCP cDNA sequence generated by this PCR reaction, MCP1 fragment, spans nucleotide nos. 41 to 943 (SEQ ID NO:11) (D. M. Lublin et al., supra). MCP1 encodes amino acid sequence corresponding to the extracellular domain of the MCP protein. It contains regions for signal peptide (SP), short consensus repeat SCR 1–4 and portion of the serine and threonine rich region (ST).

For the construction of the MCP-pG3N plasmid, MCP1 fragment was cleaved with EcoRI and SalI restriction endonucleases, gel purified and subcloned into pG3N plasmid that was treated with the same set of restriction enzymes. The treatment of MCP1 fragment with SalI resulted in the cleavage of all of its ST coding sequence other than that encoding the first three amino acids.

B. Construction of MCP-DAF expression vectors.

PCR was used to synthesize a cDNA segment, DAF2 fragment, encoding amino acid sequence corresponding to the extracellular domain of DAF protein for the construction of MCP-DAF pG3N plasmid. A plasmid containing cDNA (M. E. Medof et al., supra.) encoding amino acid sequence corresponding to the DAF protein was used in the PCR reaction described below. The primers, DAF-N5, 5'—CCT CTA GAG TCG ACT GAC TGT GGC CTT CCC CCA GAT GTA—3'(SEQUENCE ID NO:3) and DAF-C5, 5'—TCT AGA GCA TGC GAA TTC TCA ACG GGT AGT ACC TGA AGT GGT TCC—3'(SEQUENCE ID NO:4) were used as the forward and the reverse primers respectively. There was a SalI restriction site added to the 5' end of the DAF-N5 primer. A stop codon for protein translation was added to the 5' end of the DAF-C5 primer. After the stop codon, two restriction sites, EcoRI and SphI, were also introduced. Thus, the DAF2 fragment is bracketed by SalI at 5' end and a EcoRI-SphI duet at 3' end. DAF2 fragment defines a region spanning nucleotide nos. 156 to 1124 (SEQ ID NO:12) that encodes an amino acid sequence corresponding to the extracellular domain of the mature DAF protein containing SCR 1–4 and ST regions.

The construction of MCP-DAF pG3N plasmid was achieved by the ligation of DAF2 fragment and MCP-pG3N plasmid after both DNAs were cleaved with SalI and SphI restriction enzymes. The SalI site was the in-frame joint site between MCP and DAF DNA segment, thus ensuring a continuous protein translation from MCP into DAF. There was a transition of the nucleotides, ACT, into ACC at SalI site, nevertheless it still served as the codon for amino acid threonine.

MCP-DAF cDNA segment was retrieved from MCP-DAF pG3N by the treatment with EcoRI restriction enzyme and gel purification. This cDNA fragment was subsequently cloned into the EcoRI site of the pEE14 which contains the glutamine synthetase gene as a selectable marker (M. I. Cockett et al., 1990, Bio/Technology 8:662–667, herein incorporated by reference) and the p91203(B) vector which contains the dihydrofolate reductase gene as a selectable marker (G. G. Wong et al., 1985, Science 228:810–815, herein incorporated by reference) vectors. MCP-DAF P91203(B) expression vector utilizes adenovirus major late promoter to direct the expression of MCP-DAF protein and is suitable for transient expression in COS-7 and permanent expression in CHO. Expression of MCP-DAF protein in the MCP-DAF pEE14 expression vector is under the control of cytomegalovirus promoter. This vector is suitable for the establishment of a permanent CHO cell line in which the expression of MCP-DAF can be amplified in the presence of high concentration of methionine sulfoximine (M. I. Cockett et al., supra)

MCP-DAF expression vectors can direct the expression of a fusion protein with the MCP sequence at the amino-terminus and the DAF sequence at the carboxyl-terminus. The MCP portion of the fusion protein spans amino acid nos. 1 to 254 (SEQ ID NO:13) of the native mature MCP protein after the signal peptide of 34 amino acids is cleaved upon expression. It contains four SCR (1–4) regions and the first three amino acids of the ST region. The DAF portion encompasses the extracellular domain of the mature native DAF protein that ends right after the ST region (4 SCR and 1 ST regions; from amino acid nos. 1 to 324 (SEQ ID NO:14)). Overall, the MCP-DAF protein is 578 amino acid long with a predicted molecular weight of about 70 KDa. However, its actual molecular weight is higher as it also contains four N-linked glycosylation sites (3 within the MCP and 1 within the DAF) and multiple O-linked (the ST region of DAF) glycosylaton site. The recombinant chimeric protein encoded by the MCP-DAF expression vector is referred to as CAB-2.

C. Construction of MCP-MCP and MCP-1/2MCP expression vectors.

The construction of MCP-MCP and MCP-1/2MCP expression vectors was similar to that for MCP-DAF expression vectors with some exceptions described as follows.

MCP-MCP expression vectors

A MCP2 fragment was synthesized by PCR technique using MCP-N4 primer, 5'—TCG ACC TGC AGG TGT GAG GAG CCA CCA ACA TTT—3'(SEQUENCE ID NO:5) as the forward primer and MCP-UC1 primer, 5'—GCG AAT TCC TCA CAA ACT GTC AAG TAT TCC TTC CTC—3'(SEQUENCE ID NO:6) as the reverse primer. There was a PstI site added to 5' end of the MCP-N4 primer and a termination codon followed by a newly added EcoRI site was introduced at the 5' end of the MCP-UC1 primer. Thus, MCP2 fragment was framed by a PstI site at the 5' end and an EcoRI site at the 3' end. MCP2 defines a region (nucleotide nos. 146–1024; SEQ ID NO:15) that encodes an amino sequence corresponding to the extracellular domain of the mature MCP protein truncated right before the transmembrane region (amino acid nos. 1 to 293; SEQ ID NO:16). To complete the construction of MCP-MCP pG3N plasmid, the MCP-pG3N plasmid was cleaved with HindIII, end-filled with Klenow fragment, digested with PstI and finally ligated with MCP2 fragment, which had been cleaved with PstI restriction enzyme. The newly constructed MCP-MCP cDNA fragment was retrieved by EcoRI digest, gel purified, and then subcloned into the EcoRI site of the expression vectors to complete the construction of MCP-MCP expression vectors. These expression vectors direct the expression of a MCP-MCP fusion protein of 547 amino acid long with a predicted molecular weight of about 70 kDa. The actual molecular weight for MCP-MCP protein is higher as it contains six N-linked and multiple O-linked gylcosylation sites. There were two new amino acids, cysteine and arginine, added at the junction of the two MCP fragments.

MCP-1/2MCP expression vectors

The construction for MCP-1/2MCP expression vectors was identical to that for MCP-MCP expression vectors except that a different forward primer, MCP-N5, 5'—TCG ACC TGC AGG AAG GTT TTG TGT ACA CCA CCT—3'(SEQUENCE ID NO:7), was used for the synthesis of 1/2MCP DNA segment. 1/2MCP fragment spans nucleotide nos. 518 to 1024 (SEQ ID NO:17) and encodes amino acid sequence defining the SCR3, SCR4 and ST regions(amino acid nos. 124–293; SEQ ID NO:18) of the MCP protein. MCP-1/2MCP expression vectors direct the expression of MCP-1/2MCP protein of 385 amino acids long. MCP-1/2MCP protein has four N-linked and multiple O-linked glycosylation sites, thus its actual molecular weight is higher than the predicted 46 kDa.

D. Construction of DAF-MCP expression vectors.

A DAF DNA fragment, DAF1, was synthesized by PCR technique for the construction of DAF-pII SK plasmid that was used for the engineering of recombinant DAF-MCP expression vectors. The following primers were used: forward primer, DAF-N2, 5'—CGG AAT TCC ATG ACC GTC GCG CGG CCG AGC GTG—3'(SEQUENCE ID NO:8) and a reverse primer, DAF-C2R, 5'—ACC TGC AGG TTT TCC TCT GCA TTC AGG TGG T—3'(SEQUENCE ID NO:9). Restriction sites, EcoRI and PstI, were introduced to the 5' ends of DAF-N2 and DAF-C2R primers, respectively. DAF1 encompasses from nucleotide nos. 52 to 911 (SEQ ID NO.:19) of the DAF gene and encodes the amino acid sequence corresponding to the extracellular domain of the mature DAF protein truncated right before the ST region.

DAF-MCP pII SK plasmid was constructed by the ligation of PstI- and SmaI-treated DAF-pII SK vector and a MCP3 fragment that was treated with PstI. MCP3 fragment was the PCR product using a forward primer, MCP-4.2, 5'—TCG ACC TGC AGA GGA GCC ACC AAC ATT TGA AGC T—3'(SEQUENCE ID NO:10), with a PstI at the 5' end, and a reverse primer, MCP-UC1, described earlier. DAF-MCP cDNA fragment was retrieved from DAF-MCP pII SK plasmid after cleavage with EcoRI, gel purified, and then subcloned into the EcoRI site of pEE14 and P91023(B) (Wong et al., supra) expression vectors.

DAF-MCP expression vectors direct the synthesis of a DAF-MCP protein of 546 amino acid long. There are two exogenous amino acids, serine and threonine introduced at the junction between DAF and MCP due to vector construction. This protein has a predicted molecular weight of about 66 kDa exclusive of the added weight contributed by four N-linked (one within DAF and three within MCP) and multiple O-linked (located at ST region of MCP) glycosylations.

E. Cell culture and transfections.

Transfection of COS-7 cells was carried out using lipofectin (GIBCO, Gaithersburg, Md.) following the protocol recommended by the manufacturer. Briefly, the day before transfection, COS-7 cells were subcultured in new dishes (60 mm) at a cell density which would give about 70 to 80% confluency the following day. Just before transfection, the COS-7 cells were washed twice with opti-MEM medium (GIBCO) without serum. Three ml of opti-MEM medium containing 5 to 10 µg of expression vector and 20 µg of lipofectin was added to the washed COS-7 monolayer. Tranfection was allowed to take place for 6 hours at 37° C. in a $CO_2$ incubator. The transfection solution was then removed and replaced with fresh opti-MEM supplemented with 10% fetal bovine serum, 50 µg/ml streptomycin and 50 U/ml penicillin. The transfected COS-7 cells were then incubated without disturbance at 37° C. for an additional three days. The culture supernatant was collected and briefly spun to remove dead cells before conducting evaluation of biological activity.

CHO-K1 (ATCC No. CCL61) was used to establish permanent cell line expressing MCP-DAF, MCP-MCP, MCP-1/2MCP and DAF-MCP. Briefly, CHO-K1 cells were transfected with expression vectors using lipofectin as described above except that cell confluency was at about 20% before transfection and transfectants were maintained in GMEM-S medium (Glasgow MEN, without L-glutamine and tryptose phosphate broth, supplemented with 10% dialyzed fetal bovine serum, non-essential amino acids, 1 mM sodium pyruvate, 60 µg/ml L-glutamate, 60 µg/ml L-asparagine, 7 µg/ml of each of the nucleosides, 50 µg/ml streptomycin and 50 units/ml penicillin). Transfectants expressing the novel proteins were isolated and subcultured in GMEM-S medium with increasing concentration of methionine sulfoximine. CHO-K1 clones expressing the protein chimeras of the invention were then isolated by two rounds of limiting dilution cloning. Culture supernatants containing the product expression vector derived from the CHO-K1 transfectants, i.e., the CAB-2 protein, were used for purification by the methods described below.

EXAMPLE 2

Microcarrier culture for large scale production of CAB-2

A microcarrier culture method was developed with the CHO-K1 transfectant cell line expressing the recombinant CAB-2 protein.

After amplification of transfected CHO-K1 cells and cloning by limiting dilution, cells were initially cultured and expanded in T-flasks in Dulbecco's modified Eagle's medium (DMEM) supplemented with 10% fetal bovine serum (FBS), sodium pyruvate, non-essential amino acids, glutamine, asparagine, nucleosides, penicillin-streptomycin, and methionine sulfoximine (selection medium). Microcarrier cultures were prepared using 12-liter Nalgene vessels outfitted with Bellco overhead drive impeller assemblies, overlay gas addition ports, and sparge tubes. Cultisphere-G microcarriers were employed at 2.5 g/l, and washed three times with PBS and once with serum-free IMDM prior to use. Cells from twenty T150 flasks were washed with phosphate buffered saline (PBS), detached from the plates by trypsinization, and seeded into the 12-liter vessels at approximately $10 \times 10^4$ cells/ml. The medium used was IMDM with 10% bovine calf serum and penicillin-streptomycin (growth medium). Spinner vessels were fed every 2–3 days with growth medium by allowing the microcarriers to settle, removing 10 liters of medium, and replacing with 10 liters of fresh growth medium. Cell densities were monitored by counting nuclei in a sample of the cell culture, a process which involved staining microcarriers with a solution of 0.1M citric acid, 0.1% crystal violet, followed by incubation for one hour at 37° C. and enumeration using a hemocytometer. Values for pH, $pCO_2$, and $pO_2$ were monitored with a Corning model 170 blood gas analyzer. Oxygen concentration was maintained using a 40% oxygen, 5% $CO_2$, balance $N_2$ gas mixture at a rate of 10–50 ml/min through a glass sparger.

When the culture attained stable cell density (after 15–20 days growth, at cell densities of $3-10 \times 10^6$ cells/ml), production phase was initiated. This was done by replacing the growth medium with protein-free production medium, which contained 1 mM sodium butyrate and penicillin-streptomycin. For the next 10–14 days, ten liters of culture medium was replaced with fresh production medium each day. Harvested supernatants were stored at 4° C. until the culture was terminated.

Figure 4:
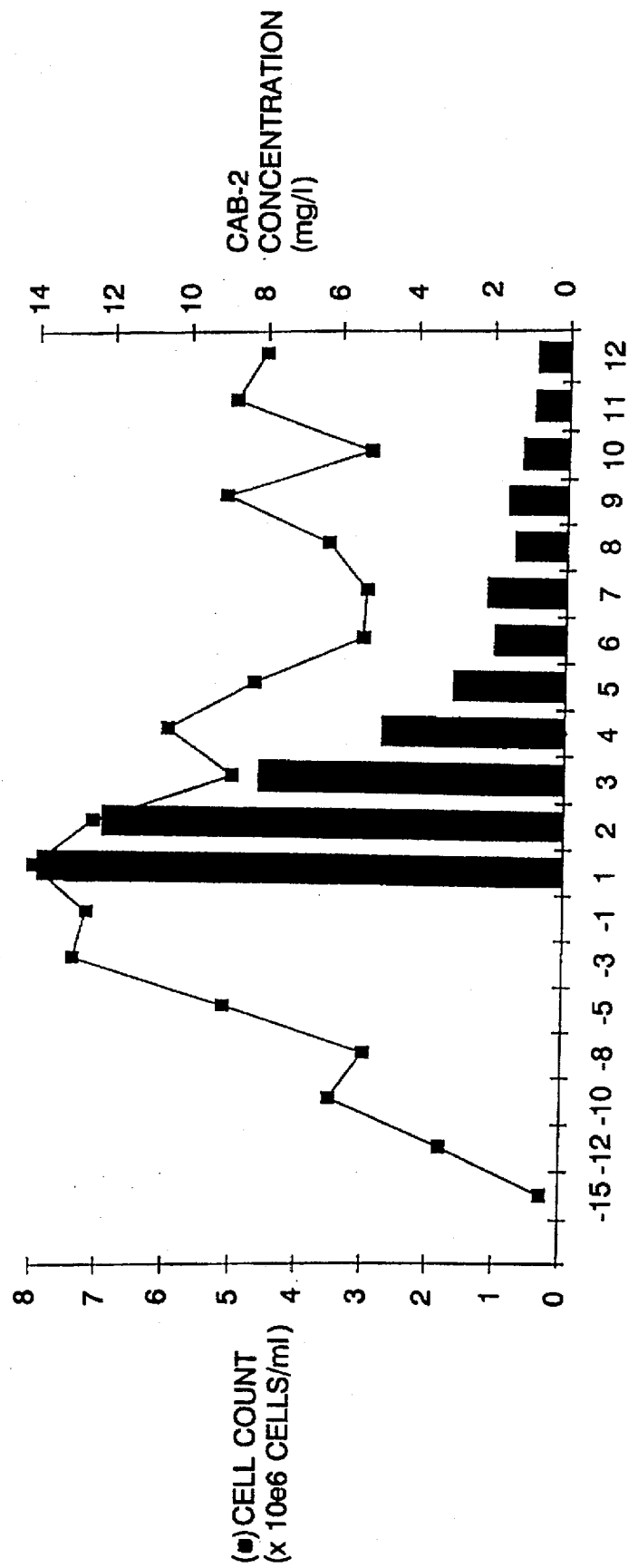

Results from a typical large-scale culture are presented in FIG. 4. The cell density was found to increase from $8 \times 10^4$ cells/ml to a density of $8 \times 10^6$ cells/ml in 15 days. Following the initiation of production phase, the cell counts dropped steadily over 12 days. FIG. 4 also showns the concentration of CAB-2 protein in each culture harvest. Conditioned medium was filtered using a Pelicon system (Millipore, Bedford, Mass.) using a 0.45 micron filter cartridge according to instructions supplied by the manufacturer. The medium was then concentrated 20–30 fold using the Pelicon ultrafiltration system with a 10,000 molecular weight cutoff membrane. Medium concentrates were stored at −70° C. until used.

EXAMPLE 3

Affinity Purification of CAB-2 from Culture Supernatants

Figure 5:
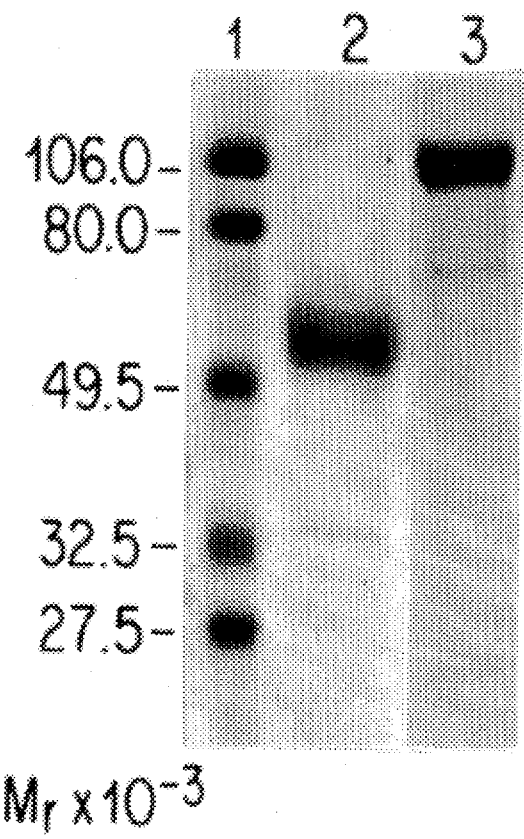

Small scale purification of the CAB-2 protein was achieved by immunoaffinity chromatography using an anti-MCP monoclonal antibody, e.g., GB24. Antibody was immobilized via the carbohydrate moiety using Carbo-link Sepharose (Pierce, Cat. #20392G). Supernatants from cultures of the CAB-2-producing recombinant CHO line were passed through a 35 ml column of GB24-Sepharose resin. The column was washed with PBS to remove any unbound proteins. CAB-2 was eluted from the column with 0.1M glycine pH 2.5. Fractions were collected and immediately neutralized with 1/10 volume of 1M Tris buffer, pH 8.5. Fractions containing protein were pooled, dialysed in PBS and concentrated. The protein was electrophoresed on a 10% polyacrylamide SDS gel (see FIG. 5). A single protein species of approximately 110 kDa was detected. This is the expected size of the CAB-2 protein, based on its deduced amino acid sequence and predicted glycosylation.

EXAMPLE 4

Chromatographic Purification of CAB-2 from Microcarrier Culture Supernatants A 7-step procedure for the purification of CAB-2 from serum-free culture supernatants was established and scaled-up to the 100 mg scale. Purification conditions are detailed, followed by the recovery results and the endotoxin reduction levels (see FIG. 6 and Table 3 which shows the degree of purification and percentage yield of CAB-2 protein after each chromatographic step). In the representative purification shown in Table 3, the purity level of the final sample was approximately 93% with an endotoxin level of 0.045 endotoxin units (EU)/mg CAB-2 and an overall CAB-2 recovery of 24%. The recovery in this run was low due to an unexplained loss of CAB-2 in the final step. Recoveries of CAB-2 are routinely 35–50%.

Step 1: Contaminant Precipitation

Concentrated conditioned media was diluted 1:1 with Q Sepharose equilibration buffer (25 mM piperazine pH 5.0) and the pH was adjusted to 5.0. A fine precipitate was formed and was filtered through a precipitate-adsorbing agent (Celite 621, Aldrich) using a Buchner funnel.

Step 2: Anion Exchange Chromatography

Q Sepharose FF resin (Pharmacia) was packed as a 1.1 liter column (9.0×17.3 cm). The resin was depyrogenated with 0.5N NaOH and equilibrated with 25 mM piperazine pH 5.0. The filtered pool from step 1 was loaded onto the column at 10 mg total protein (TP) per ml resin. The column was washed with equilibration buffer (25 mM piperazine pH 5.0) to remove contaminants. The column was then washed with 200 mM NaCl buffer, which resulted in the elution of two peaks, the first containing CAB-2 and the second containing the media color additive (phenol red).

Step 3: Immobilized Metal Affinity Chromatography

Chelate Sepharose FF (Pharmacia) was packed to a bed volume of 50 ml (2.2×13 cm). The resin was depyrogenated with 0.5N NaOH and washed with $dH_2O$. The resin was charged with 100 ml 0.3M $ZnCl_2$, washed with $dH_2O$ and equilibrated with 25 mM MES pH 6.0 containing 0.2M NaCl. The Q Sepharose pool (the material eluted from the Q Sepharose column which contained the CAB-2 protein) was brought to 25 mM MES pH 6.0 and loaded at 20 mg TP per ml of resin onto the Chelate column at a rate of 150 cm/hr. The column was washed with equilibration buffer, and CAB-2 was collected in the flowthrough.

Step 4: Phenyl Hydrophobic Interaction Chromatography

A 290 ml (4.4×19.1 cm) TosoHaas Phenyl 650M HIC column was depyrogenated with 0.5N NaOH and equilibrated with 25 mM phosphate pH 7.0 containing 3M NaCl. The flowthrough pool from Step 3 was adjusted to 25 mM phosphate pH 7.0 and 3M NaCl, and loaded onto the column at 3.5 mg TP per ml of resin. Following an equilibration buffer wash, the CAB-2 was eluted with 25 mM phosphate pH 7.0 containing 1M NaCl.

Step 5: Butyl Hydrophobic Interaction Chromatography

A 110 ml column (3.2×13.7 cm) containing TosoHaas Butyl 650M HIC resin was depyrogenated with 0.5N NaOH and equilibrated with 25 mM phosphate pH 7.0 containing 3M NaCl. The elution pool from Step 4 was adjusted to 3M NaCl and pH 7.0 and then loaded onto the column. The column was washed with equilibration buffer and the CAB-2 then eluted with 25 mM phosphate pH 7.0 containing 1M NaCl.

Step 6: Diafiltration and Concentration

The elution pool from Step 5 was concentrated 5–6 fold using a Mini-ultrasette tangential flow system from Filtron containing a 10 kDa MWCO Omega membrane. The pool was then diafiltered with 4–5 sample volumes of PBS.

TABLE 3

CAB-2 Purification Run 062194
(started with 250 mg CAB-2 in conditioned media)

| Step | Percent Purity mg CAB-2/mg TP (×100) | Percent Overall Recovery* | Endotoxin Level EU per mg CAB-2 |
|---|---|---|---|
| Starting Media | 1 | — | — |
| 1-contaminant precipitation. | 1 | 110.1 | 72.34 |
| 2-anion exchange | 22 | 56.7 | 73.95 |
| 3-IMAC | 16 | 43.2 | 109.71 |
| 4-phenyl HIC | 42 | 40.7 | 27.60 |
| 5-butyl HIC | 49 | 38.9 | 7.61 |
| 6-diafiltration and concentration | NA | NA | 4.10 |
| 7-post-detoxigel | 93 | 23.7* | 0.05 |

Step 7: Endotoxin Removal and Final Concentration

Although the phenyl and butyl HIC steps significantly reduce the endotoxin levels in the sample (see Table 3), the sample was further depyrogenated by eluting twice through a Pierce endotoxin affinity resin. The 5 ml column (1×6 cm) was first stripped of endotoxin with 1% deoxycholate, then equilibrated with endotoxin-free PBS. The CAB-2 was passed through the column in sterile PBS. Finally, the CAB-2 was concentrated with an Amicon Centriprep 10 (previously depyrogenated with 70% alcohol). The final endotoxin concentration was 0.045 EU per mg CAB-2.

EXAMPLE 5

Detection of CAB-2 by ELISA

Figure 7:
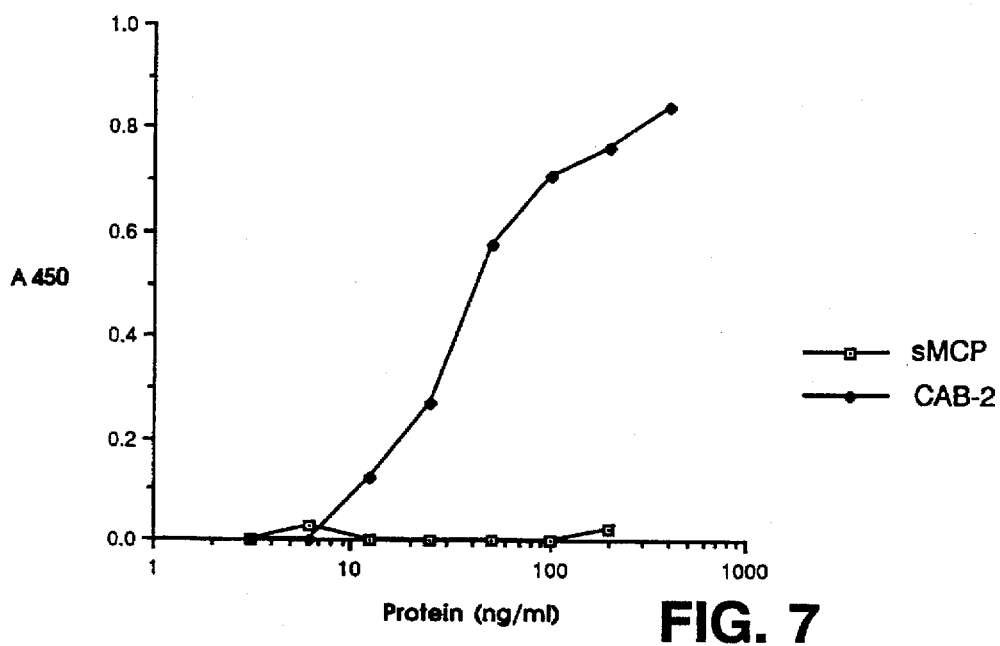

An ELISA assay was developed using antibodies directed against membrane cofactor protein (MCP) and decay accelerating factor (DAF). A rabbit anti-MCP polyclonal antiserum was generated by immunization of rabbits with soluble MCP (sMCP). IgG was purified from the antiserum by immobilized Protein A affinity chromatography. An aliquot (50 µl) of polyclonal anti-MCP IgG at 2 µg/ml was added to 96-well ELISA plates, and the plates were incubated overnight at 4° C. After blocking the plates with 1% BSA, 0.1% Tween in PBS, purified sMCP or CAB-2 proteins were added at various concentrations in blocking buffer and incubated for 1 h at 37° C. A murine anti-DAF monoclonal antibody (BRIC 216, Harlan Bioproducts Cat. #MCA914) was added at 1 µg/ml and incubated for 1 h at 37° C. An HRPO-conjugated goat anti-mouse IgG tertiary antibody was added at 1:1000 dilution and incubated for 1 h at 37° C. An enzyme substrate (TMB, Pierce Chemical Co., Rockford, Ill., Cat. #34021) was added and the reaction stopped with 2M $H_2SO_4$. $OD_{450}$ values were determined on an ELISA plate reader. Data shown in FIG. 7 demonstrate that the CAB-2 protein was detected by the two antibody sandwich ELISA, indicating that the protein expresses both MCP and DAF domains. Soluble MCP, on the other hand, was not detected by this combination of antibodies.

EXAMPLE 6

Figure 8:
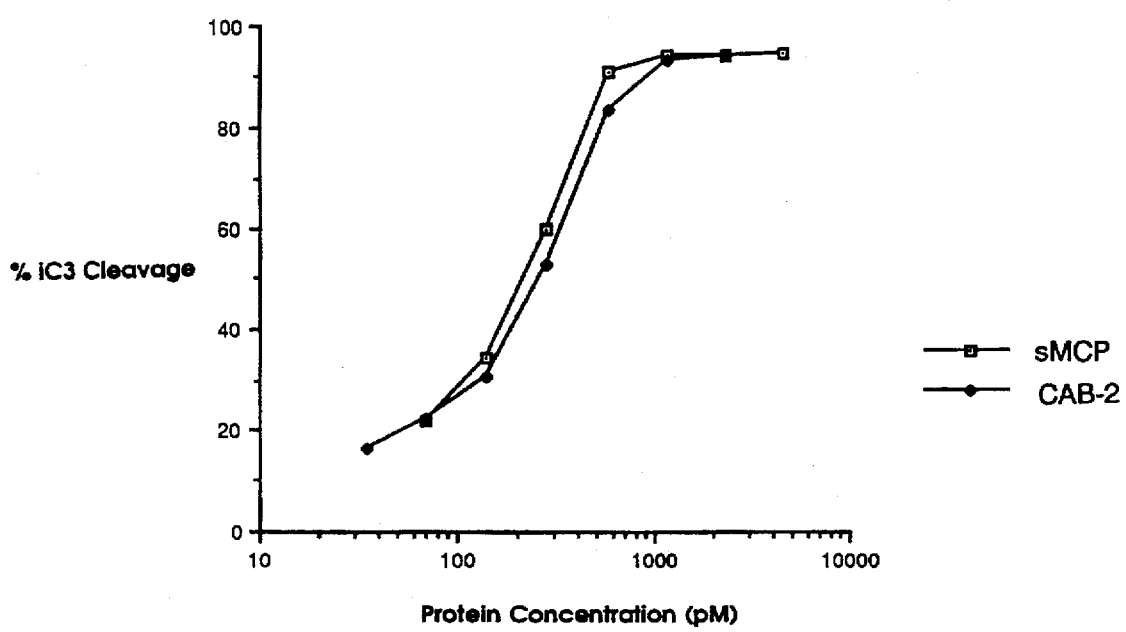

Demonstration of in vitro Activity of CAB-2 Chimeric Protein Cofactor Activity An assay for determination of Factor I cofactor activity was performed as described by Seya et al. (J. Exp. Med., 1986, 163:837, herein incorporated by reference). Purified human C3 protein (Quidel, San Diego, Calif., Cat. #A401)

at 1 mg/ml was incubated with an equal volume of 4M KBr for 1 h at 37° C. to cleave the internal thioester bond. The resulting protein (iC3) was dialyzed overnight in phosphate buffered saline. Aliquots of iC3 (8 µl) were mixed with 2 µl of 66 µg/ml purified Factor I (Quidel, San Diego, Calif., Cat #A411) and 6 µl volumes of varying concentrations of purified CAB-2 or sMCP protein in buffer (1:6 diluted PBS, 0.5% NP-40). The mixture was incubated for 1 h at 37° C. and the reaction was stopped by adding an equal volume of SDS sample buffer (100 mM Tris pH 6.8, 20 mM dithiothreitol, 20% sucrose, 2% SDS, 0.01% Bromphenol blue). The samples were boiled for 5 min. and electrophoresed on a 10% polyacrylamide gel by standard procedures (Laemmli, U., 1970, Nature 227:680). The gels were stained with 0.05% Coomassie blue, destained and dried. Percentage cleavage of the alpha chain of iC3 was quantified by scanning densitometry (XRS OmniMedia scanner). Results shown in FIG. 8 indicate that the CAB-2 protein has factor I cofactor activity comparable to that of the soluble MCP recombinant protein.

Decay Accelerating Factor Activity

Figure 9:
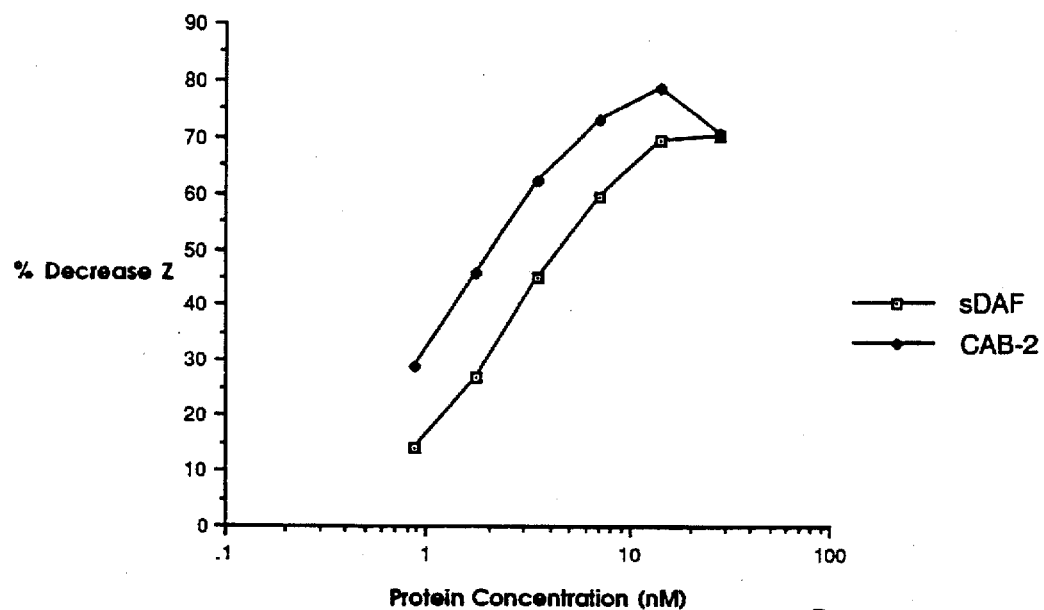

The measurement of decay accelerating activity of the chimeric CAB-2 protein was carried out as follows. Commercially available sheep RBC sensitized with IgM, C1 and C4 (EAC14, Diamedix Cat #789-053) were used as a source of cell membrane-deposited C4b. The RBC were diluted to $2.5 \times 10^8$/ml in buffer (2.5 mM veronal, 75 mM NaCl, 0.15 mM $CaCl_2$, 1 mM $MgCl_2$, 0.1% gelatin, 2.5% dextrose) and preincubated at 30° C. for 5 min. Purified C2 (Quidel, San Diego, Calif., Cat #A403) diluted to 33 U/ml in the same buffer was added to the cells and incubated for 4 min at 30° C. The RBC were immediately washed in 10 mM EDTA buffer (2.5 mM veronal, 75 mM NaCl, 0.1% gelatin, 10 mM EDTA) and resuspended in the same buffer. Aliquots (50 µl) of the sensitized RBC were transferred to tubes containing varying concentrations (in 50 µl) of either soluble DAF or CAB-2 protein. The samples were allowed to decay for 15 min at 30° C., after which the lytic sites were developed by adding 0.5 ml of guinea pig complement (1:50 diluted serum) in 40 mM EDTA buffer (2.5 mM veronal, 75 mM NaCl, 0.1% gelatin, 40 mM EDTA). After incubation for 30-40 min at 37° C., the cells were centrifuged and the $OD_{405}$ of the supernatants determined. The number of lytic sites/cell (Z) were determined from standard tables and the decay accelerating activity determined by the decrease of the Z values in comparison to a positive control (sample without DAF or CAB-2). Results, shown in FIG. 9, demonstrate that the CAB-2 protein possesses decay accelerating activity comparable to that of sDAF.

Inhibition of Complement-Mediated Lysis, Classical Activation

Figure 10:
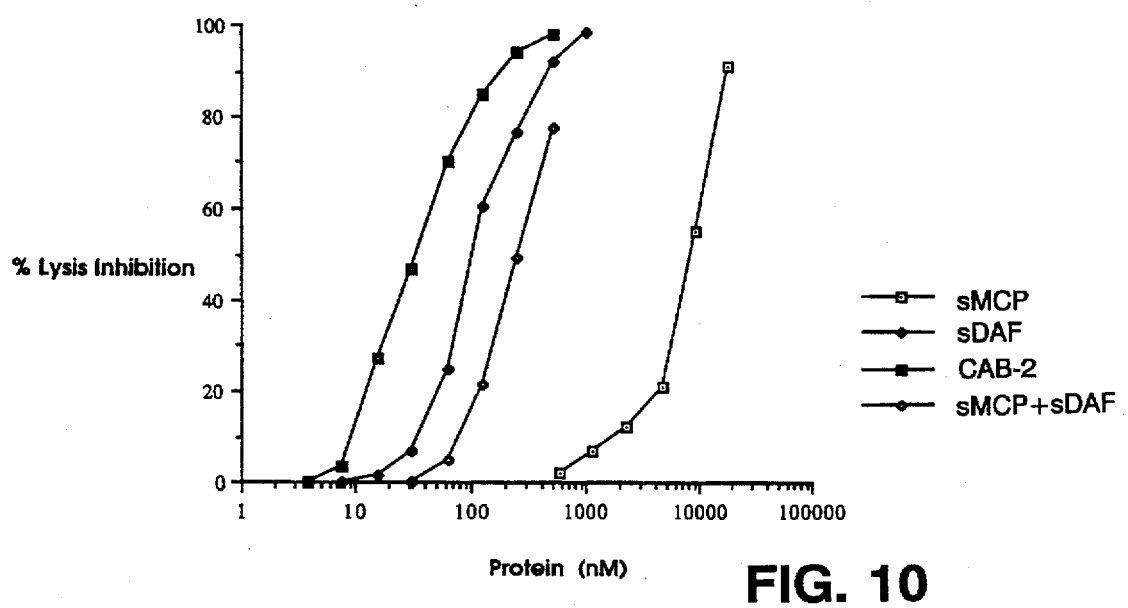

The ability of chimeric CAB-2 protein to inhibit complement-mediated cell lysis via the classical pathway was determined by a hemolytic assay using IgM-sensitized sheep RBC. Commercially available IgM-sensitized sheep RBC (Diamedix, Cat. #789-001) in 100 µl aliquots were added to 50 µl of either purified sMCP, purified sDAF or CAB-2 protein at varying concentrations in gelatin veronal buffer ($GVB^{+2}$) (Sigma, Cat. #G-6514). Human serum (50 µl) diluted 1:50 in $GVB^{+2}$ was immediately added as the source of complement. Cells were incubated for 30 min at 37° C., centrifuged, and the supernatants transferred to multiwell plates. The $OD_{405}$ of the supernatants was measured and the inhibition of hemolysis determined for each protein. The results shown in FIG. 10 indicate that both sMCP and sDAF can individually inhibit complement-mediated cell lysis via the classical pathway, although at different potencies (XC50 of 7000 nM and 100 nM respectively). When both sMCP and sDAF were added together on a equal molar basis, their additive potency did not increase (IC50 of 200 nM). In contrast, CAB-2, which possesses both cofactor and decay accelerating activities, inhibited cell lysis ($IC_{50}$ of 30 nM) with a potency significantly greater than either sMCP alone (230-fold), sDAF alone (3-fold), or both factors in combination (6-fold).

Inhibition of Complement-Mediated Lysis, Alternative Activation

Figure 11:
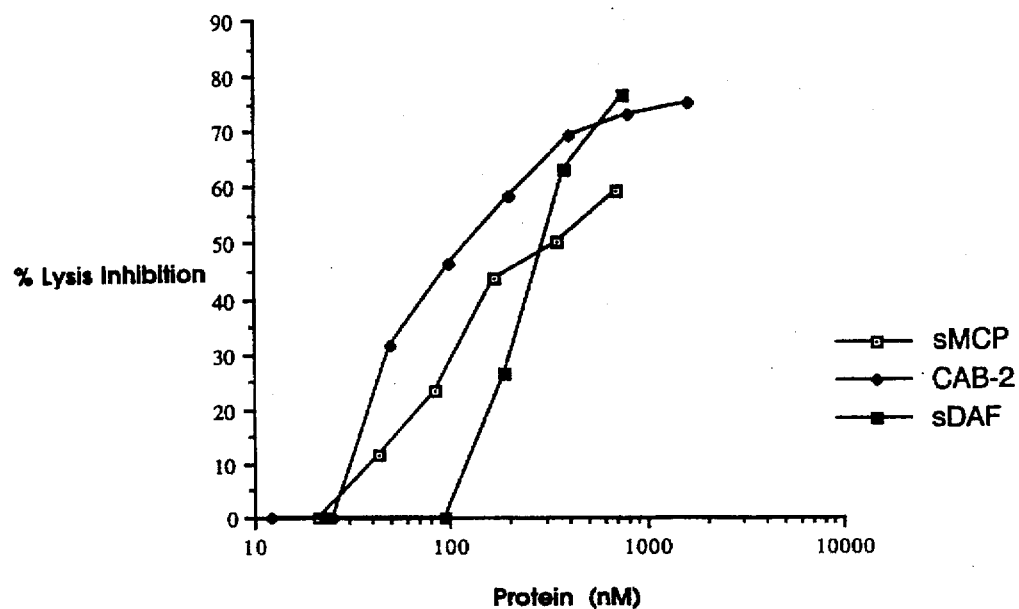

Complement-mediated cell lysis via the alternative pathway was determined by the use of unsensitized guinea pig RBC, which induce alternative pathway complement activation. Guinea pig blood was collected in a heparinized syringe and washed twice with PBS. RBC were resuspended at $2 \times 10^8$/ml in assay buffer ($GVB^{+2}$ containing 8 mM EGTA and 1.5 mM additional $MgCl_2$). Cells (100 µl) were mixed with 50 µl volumes of purified sMCP, sDAF or CAB-2 at various concentrations in assay buffer. Undiluted human serum (50 µl) was added as a source of complement. Samples were incubated for 30 min at 37° C. and centrifuged. Supernatants were transferred to microtiter plates and their $OD_{405}$ measured. Results are shown in FIG. 11. It was observed that the ability of sMCP to inhibit alternative pathway-mediated hemolysis is greater than its activity in the classical hemolytic assay ($IC_{50}$ of 350 nM and 7000 nM respectively). However, the inhibitory activity of CAB-2 protein in this assay is greater than that of sMCP and sDAF ($IC_{50}$ 100 nM).

Inhibition of C5a generation

Figure 12:
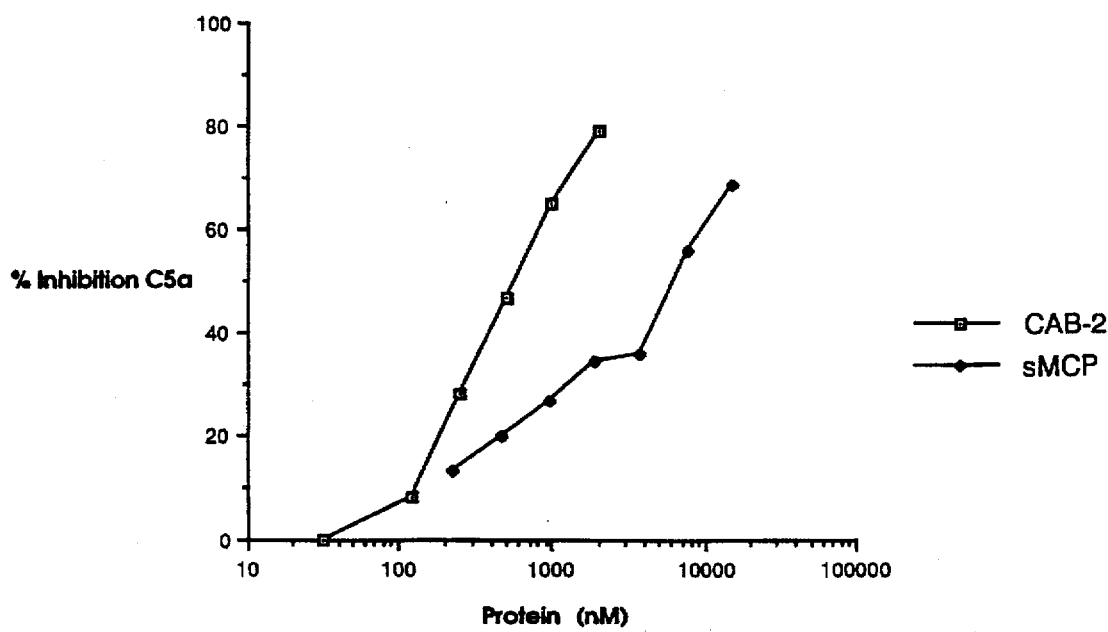

The complement inhibitory activity of CAB-2 was also tested by specifically assaying the inhibition of C5 convertase via the production of C5a. Human serum, diluted 1:8 in $GVB^{+2}$, was used as the source of complement. Purified sMCP or CAB-2 protein were added to the serum at various concentrations. The classical pathway was initiated by the addition of heat aggregated rabbit IgG at 100 µg/ml. After incubation for 1 h at 37° C., the reaction was stopped by addition of 10 mM EDTA. Detection of C5a in the reaction was performed by competition radioimmunoassay using a commercially available C5desarg kit (Amersham, Cat #RPA520). Results for zymosan-induced C5a generation are shown in FIG. 12. CAB-2 more potently inhibits C5a production via the alternative pathway than does sMCP ($IC_{50}$ 300 nM and 5000 nM respectively).

EXAMPLE 7

Pharmacokinetics of CAB-2

Figure 13:
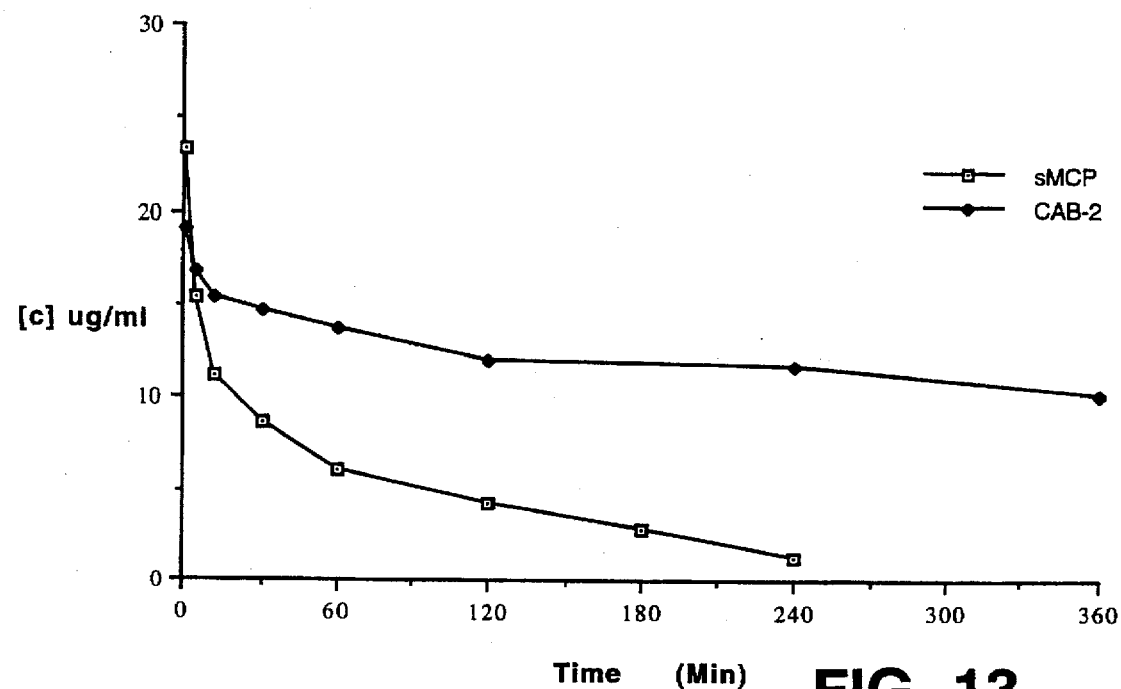

The pharmacokinetic behavior of purified CAB-2 protein was determined in rats and compared to that of sMCP. Female Sprague-Dawley rats, 250-300 g in weight, were anesthetized by intraperitoneal (i.p.) injection of a 40 g/kg dose of sodium pentobarbital. Animals were catheterized via the femoral artery and femoral vein. A dose of 1 mg/kg body weight of either sMCP or CAB-2 in saline was injected via the venous catheter. At various times after injection (T=1, 5, 12, 30 min, and 1, 2, 3, 4 hr) an aliquot (0.2-0.3 ml) of blood was drawn via the arterial catheter into a heparinized syringe and immediately replaced with an equal volume of saline. Blood samples were immediately centrifuged and the plasma removed and frozen. Plasma levels of protein were determined by ELISA using a rabbit anti-MCP polyclonal antibody as capture antibody and a HRPO-conjugated anti-MCP monoclonal antibody (GB24) as secondary antibody. Standard curves using purified sMCP or CAB-2 were used to quantitate the concentrations of the respective proteins in the blood samples. The results are shown in FIG. 13. Clearance rates for CAB-2 were significantly slower compared to sMCP (T½ B of 560 min and 80 min, respectively). In addition, loss of recombinant protein from plasma in the distribution (α) phase, determined from the area under the clearance curves, was less in the case of CAB-2 (6%) than for sMCP (16%). Increased duration of CAB-2 in plasma makes this protein a better candidate for clinical therapy.

Figure 14:
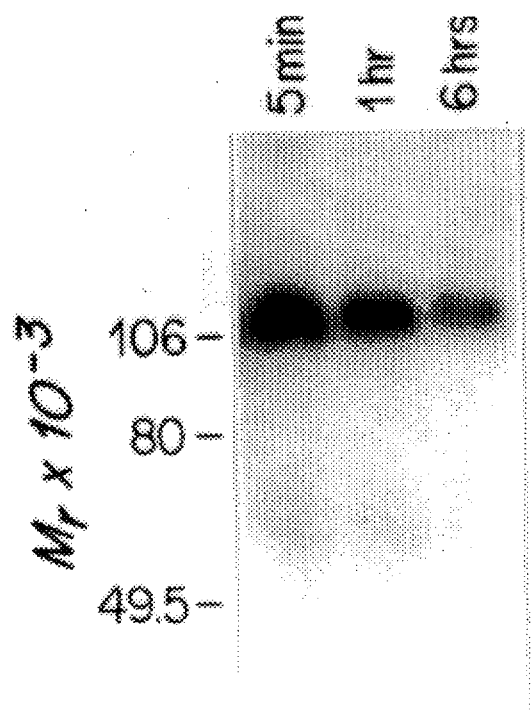

The structural integrity of the CAB-2 protein after injection in vivo was determined by using $^{125}$I-labeled CAB-2. After i.v. injection of $^{125}$I-CAB-2, aliquots of serum were obtained from the rats at various times. The serum samples were electrophoresed on a 10% polyacrylamide SDS gel and autoradiographed. The CAB-2 protein showed no detectable degradation after 6 hours in vivo (FIG. 14).

EXAMPLE 8

In vivo efficacy of CAB-2 in the reversed passive Arthus model

Figure 15:
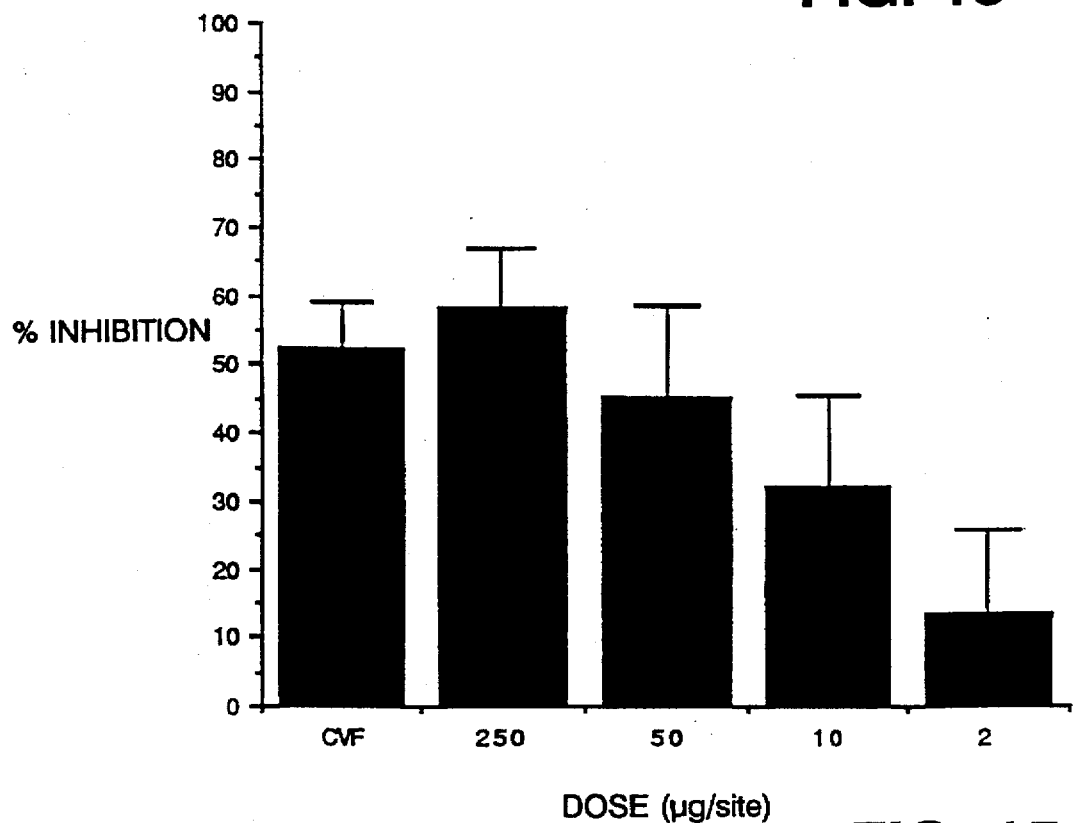

Male guinea pigs (300–350 g) were anesthetized by i.p. injection of 40 mg/kg of sodium pentobarbital. Animals were injected i.v. with a dose of 20 mg/kg of ovalbumin along with 1 µCi of 125I-labeled BSA. Animals were then immediately challenged by i.d. injection of 10 mg polyclonal anti-ovalbumin antibody, either alone or mixed with various doses of CAB-2, in the dorsal region. The total volume injected i.d. was 100 ml. After three hours, animals were sacrificed by $CO_2$ inhalation. The skin was removed, the antibody challenge sites isolated by a ⅝ inch biopsy punch, and the biopsies counted. Inhibition of the inflammatory response was measured by comparing the leakage of $^{125}$I-BSA into the skin (CPM per challenge site) of sites co-injected with CAB-2 versus sites without CAB-2. Another set of animals were pre-treated by i.p. injection of 200 U/kg cobra venom factor (CVF) 24 hours before initiation of the Arthus response. This treatment results in de-complementation of the animal, and is a positive control for the effect of complement inhibition in this model. As shown in FIG. 15, injection of CAB-2 inhibited the reversed passive Arthus reaction in a dose-dependent manner. The maximum inhibition observed was comparable to that of CVF pre-treatment.

Other Embodiments

Also within the invention are analogs of the chimeric proteins of the invention.

Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. Table 2 lists a number of conservative amino acid substitutions.

TABLE 2

CONSERVATIVE AMINO ACID REPLACEMENTS

| For Amino Acid | Code | Replace With |
|---|---|---|
| Alanine | A | D—Ala, Gly, Aib, β-Ala, Acp, L—Cys, D—Cys |
| Arginine | R | D—Arg, Lys, D—Lys, homo-Arg, D-homo-Arg, Met, Ile, D—Met, D—Ile, Orn, D—Orn |
| Asparagine | N | D—Asn, Asp, D—Asp, Glu, D—Glu, Gln, D—Gln |
| Aspartic Acid | D | D—Asp, D—Asn, Asn, Glu, D—Glu, Gln, D—Gln |
| Cysteine | C | D—Cys, S—Me—Cys, Met, D—Met, Thr, D—Thr |
| Glutamine | Q | D—Gln, Asn, D—Asn, Glu, D—Glu, Asp, D—Asp |
| Glutamic Acid | E | D—Glu, D—Asp, Asp, Asn, D—Agn, Gln, D—Gln |
| Glycine | G | Ala, D—Ala, Pro, D—Pro, Aib, β—Ala, Acp |
| Isoleucine | I | D—Ile, Val, D—Val, AdaA, AdaG, Leu, D—Leu, Met, D—Met |
| Leucine | L | D—Leu, Val, D—Val, AdaA, AdaG, Leu, D—Leu, Met, D—Met |
| Lysine | K | D—Lys, Arg, D—Arg, homo-Arg, D-homo-Arg, Met, D—Met, Ile, D—Ile, Orn, D—Orn |
| Methionine | M | D—Met, S—Me—Cys, Ile, D—Ile, Leu, D—Leu, Val, D—Val |
| Phenyl-alanine | F | D—Phe, Tyr, D—Thr, L—Dopa, His, D—His, Trp, D—Trp, Trans-3,4, or 5-phenylproline, AdaA, AdaG, cis-3,4, or 5-phonylproline, Bpa, D—Bpa |
| Proline | P | D—Pro, L—I-thioazolidine-4-carboxylic acid, D-or L-1-oxazolidine-4-carboxylic acid (Kauer, U.S. Pat. (4,511,390) |
| Serine | S | D—Ser, Thr, D—Thr, allo-Thr, Met, D—Met, Met(O), D—Met(O), L—Cys, D—Cys |
| Threonine | T | D—Thr, Ser, D—Ser, allo-Thr, Met, D—Met, Met(O), D—Met(O), Val, D—Val |
| Tyrosine | Y | D—Tyr, Phe, D—Phe, L—Dopa, His, D—His |
| Valine | V | D—Val, Leu, D—Leu, Ile, D—Ile, Met, D—Met, AdaA, AdaG |

What is claimed is:

1. A soluble chimeric protein comprising a first soluble polypeptide which inhibits complement activation linked to a second soluble polypeptide which inhibits complement activation, wherein said first and second polypeptides are derived from the same or different member of the regulator of complement activation (RCA) family and wherein said first polypeptide is linked to said second polypeptide by a peptide bond.

2. The chimeric protein of claim 1, wherein said first polypeptide is derived from membrane cofactor protein, and said second polypeptide is derived from decay accelerating factor.

3. The chimeric protein of claim 1, wherein the members of the regulator of complement activation (RCA) family are selected from the group consisting of membrane cofactor protein, decay accelerating factor, complement receptor 1, factor H, and C4b binding protein.

4. The chimeric protein of claim 3, wherein said first and said second polypeptides are different.

5. The chimeric protein of claim 4, wherein the first polypeptide comprises a fragment of membrane cofactor protein and the second polypeptide comprises a fragment of decay accelerating factor.

6. The chimeric protein of claim 5, wherein said first polypeptide comprises at least regions 2, 3 and 4 of membrane cofactor protein short consensus repeats, and said second polypeptide comprises at least regions 2, 3 and 4 of decay accelerating factor short consensus repeats.

7. A nucleic acid encoding the chimeric protein of claim 1.

8. A recombinant expression vector comprising a selectable marker and the nucleic acid of claim 7 operably linked to regulatory sequences for expression of said protein.

9. The recombinant expression vector of claim 8, wherein said regulatory sequences comprise a mammalian promoter.

10. The expression vector of claim 8, wherein said selectable marker comprises a gene encoding glutamine synthetase or a gene encoding dihydrofolate reductase.

11. A process for preparing a recombinant chimeric protein, comprising culturing a suitable host cell comprising the vector of claim 8 under conditions promoting expression and purifying said protein from said cell.

12. The process of claim 11, wherein said host cell is a bacterial cell, a yeast cell, an insect cell, or a mammalian cell.

13. The process of claim 12, wherein said mammalian cell is a chinese hamster ovary cell.

14. The process of claim 11, further comprising, following said culturing step:

(a) collecting a cell supernatant or a cell lysate of said host cell;

(b) removing acid-precipitable contaminants from said supernatant or lysate to yield a partially-purified composition;

(c) contacting said composition with an anion exchange resin to bind said chimeric protein thereto and then eluting said chimeric protein;

(d) removing metal-binding contaminants from said chimeric protein;

(e) binding said chimeric protein to a phenyl hydrophobic interaction resin and then eluting said chimeric protein;

(f) binding said chimeric protein to a butyl hydrophobic interaction resin and then eluting said chimeric protein; and (g) removing endotoxin from said chimeric protein, wherein steps d.–f. can be carried out in any order.

* * * * *

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
( A ) LENGTH: 24 base pairs
( B ) TYPE: nucleic acid
( C ) STRANDEDNESS: single ( D ) TOPOLOGY: linear ( x i ) SEQUENCE DESCRIPTION: SEQ ID NO: 1:

GGAATTCGCA TGGAGCCTCC CGGC    24

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CTATGAGGCA CTGGACGCTG GAGATTT    27

( 2 ) INFORMATION FOR SEQ ID NO: 3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CCTCTAGAGT CGACTGACTG TGGCCTTCCC CCAGATGTA    39

( 2 ) INFORMATION FOR SEQ ID NO: 4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TCTAGAGCAT GCGAATTCTC AACGGGTAGT ACCTGAAGTG GTTCC    45

( 2 ) INFORMATION FOR SEQ ID NO: 5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TCGACCTGCA GGTGTGAGGA GCCACCAACA TTT    33

( 2 ) INFORMATION FOR SEQ ID NO: 6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GCGAATTCCT CACAAACTGT CAAGTATTCC TTCCTC    36

( 2 ) INFORMATION FOR SEQ ID NO: 7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TCGACCTGCA GGAAGGTTTT GTGTACACCA CCT                33

( 2 ) INFORMATION FOR SEQ ID NO: 8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CGGAATTCCA TGACCGTCGC GCGGCCGAGC GTG                33

( 2 ) INFORMATION FOR SEQ ID NO: 9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

ACCTGCAGGT TTTCCTCTGC ATTCAGGTGG T                  31

( 2 ) INFORMATION FOR SEQ ID NO: 10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

TCGACCTGCA GAGGAGCCAC CAACATTTGA AGCT               34

( 2 ) INFORMATION FOR SEQ ID NO:11:

( i ) SEQUENCE CHARACTERISTICS:
        ( A ) LENGTH: 903 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
CGCATGGAGC CTCCCGGCCG CCGCGAGTGT CCCTTTCCTT CCTGGCGCTT TCCTGGGTTG     60
CTTCTGGCGG CCATGGTGTT GCTGCTGTAC TCCTTCTCCG ATGCCTGTGA GGAGCCACCA    120
ACATTTGAAG CTATGGAGCT CATTGGTAAA CCAAAACCCT ACTATGAGAT TGGTGAACGA    180
GTAGATTATA AGTGTAAAAA AGGATACTTC TATATACCTC CTCTTGCCAC CCATACTATT    240
TGTGATCGGA ATCATACATG GCTACCTGTC TCAGATGACG CCTGTTATAG AGAAACATGT    300
CCATATATAC GGGATCCTTT AAATGGCCAA GCAGTCCCTG CAAATGGGAC TTACGAGTTT    360
GGTTATCAGA TGCACTTTAT TTGTAATGAG GGTTATTACT TAATTGGTGA AGAAATTCTA    420
TATTGTGAAC TTAAAGGATC AGTAGCAATT TGGAGCGGTA AGCCCCCAAT ATGTGAAAAG    480
GTTTTGTGTA CACCACCTCC AAAAATAAAA AATGGAAAAC ACACCTTTAG TGAAGTAGAA    540
GTATTTGAGT ATCTTGATGC AGTAACTTAT AGTTGTGATC CTGCACCTGG ACCAGATCCA    600
TTTTCACTTA TTGGAGAGAG CACGATTTAT TGTGGTGACA ATTCAGTGTG GAGTCGTGCT    660
GCTCCAGAGT GTAAAGTGGT CAAATGTCGA TTTCCAGTAG TCGAAAATGG AAAACAGATA    720
```

|                                                                                          |     |
|------------------------------------------------------------------------------------------|-----|
| TCAGGATTTG GAAAAAAATT TTACTACAAA GCAACAGTTA TGTTTGAATG CGATAAGGGT                         | 780 |
| TTTTACCTCG ATGGCAGCGA CACAATTGTC TGTGACAGTA ACAGTACTTG GGATCCCCA                          | 840 |
| GTTCCAAAGT GTCTTAAAGT GTCGACTTCT TCCACTACAA AATCTCCAGC GTCCAGTGCC                         | 900 |
| TCA                                                                                      | 903 |

(2) INFORMATION FOR SEQ ID NO:12:

(i) SEQUENCE CHARACTERISTICS:
        (A) LENGTH: 969 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

|                                                                                          |     |
|------------------------------------------------------------------------------------------|-----|
| GACTGTGGCC TTCCCCCAGA TGTACCTAAT GCCCAGCCAG CTTTGGAAGG CCGTACAAGT                         | 60  |
| TTTCCCGAGG ATACTGTAAT AACGTACAAA TGTGAAGAAA GCTTTGTGAA AATTCCTGGC                         | 120 |
| GAGAAGGACT CAGTGACCTG CCTTAAGGGC ATGCAATGGT CAGATATTGA AGAGTTCTGC                         | 180 |
| AATCGTAGCT GCGAGGTGCC AACAAGGCTA AATTCTGCAT CCCTCAAACA GCCTTATATC                         | 240 |
| ACTCAGAATT ATTTTCCAGT CGGTACTGTT GTGGAATATG AGTGCCGTCC AGGTTACAGA                         | 300 |
| AGAGAACCTT CTCTATCACC AAAACTAACT TGCCTTCAGA ATTTAAAATG GTCCACAGCA                         | 360 |
| GTCGAATTTT GTAAAAAGAA ATCATGCCCT AATCCGGGAG AAATACGAAA TGGTCAGATT                         | 420 |
| GATGTACCAG GTGGCATATT ATTTGGTGCA ACCATCTCCT TCTCATGTAA CACAGGGTAC                         | 480 |
| AAATTATTTG GCTCGACTTC TAGTTTTTGT CTTATTTCAG GCAGCTCTGT CCAGTGGAGT                         | 540 |
| GACCCGTTGC CAGAGTGCAG AGAAATTTAT TGTCCAGCAC CACCACAAAT TGACAATGGA                         | 600 |
| ATAATTCAAG GGAACGTGA CCATTATGGA TATAGACAGT CTGTAACGTA TGCATGTAAT                          | 660 |
| AAAGGATTCA CCATGATTGG AGAGCACTCT ATTTATTGTA CTGTGAATAA TGATGAAGGA                         | 720 |
| GAGTGGAGTG GCCCACCACC TGAATGCAGA GGAAAATCTC TAACTTCCAA GGTCCCACCA                         | 780 |
| ACAGTTCAGA AACCTACCAC AGTAAATGTT CCAACTACAG AAGTCTCACC AACTTCTCAG                         | 840 |
| AAAACCACCA CAAAACCAC CACACCAAAT GCTCAAGCAA CACGGAGTAC ACCTGTTTCC                          | 900 |
| AGGACAACCA AGCATTTTCA TGAAACAACC CCAAATAAAG GAAGTGGAAC CACTTCAGGT                         | 960 |
| ACTACCCGT                                                                                | 969 |

(2) INFORMATION FOR SEQ ID NO:13:

(i) SEQUENCE CHARACTERISTICS:
        (A) LENGTH: 254 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

```
Cys Glu Glu Pro Pro Thr Phe Glu Ala Met Glu Leu Ile Gly Lys Pro
 1               5                  10                  15
Lys Pro Tyr Tyr Glu Ile Gly Glu Arg Val Asp Tyr Lys Cys Lys Lys
                20                  25                  30
Gly Tyr Phe Tyr Ile Pro Pro Leu Ala Thr His Thr Ile Cys Asp Arg
                35                  40                  45
Asn His Thr Trp Leu Pro Val Ser Asp Asp Ala Cys Tyr Arg Glu Thr
            50                  55                  60
```

```
Cys  Pro  Tyr  Ile  Arg  Asp  Pro  Leu  Asn  Gly  Gln  Ala  Val  Pro  Ala  Asn
65                  70                  75                            80

Gly  Thr  Tyr  Glu  Phe  Gly  Tyr  Gln  Met  His  Phe  Ile  Cys  Asn  Glu  Gly
               85                       90                       95

Tyr  Tyr  Leu  Ile  Gly  Glu  Glu  Ile  Leu  Tyr  Cys  Glu  Leu  Lys  Gly  Ser
              100                      105                      110

Val  Ala  Ile  Trp  Ser  Gly  Lys  Pro  Pro  Ile  Cys  Glu  Lys  Val  Leu  Cys
              115                      120                      125

Thr  Pro  Pro  Pro  Lys  Ile  Lys  Asn  Gly  Lys  His  Thr  Phe  Ser  Glu  Val
     130                      135                      140

Glu  Val  Phe  Glu  Tyr  Leu  Asp  Ala  Val  Thr  Tyr  Ser  Cys  Asp  Pro  Ala
145                           150                 155                           160

Pro  Gly  Pro  Asp  Pro  Phe  Ser  Leu  Ile  Gly  Glu  Ser  Thr  Ile  Tyr  Cys
               165                           170                           175

Gly  Asp  Asn  Ser  Val  Trp  Ser  Arg  Ala  Ala  Pro  Glu  Cys  Lys  Val  Val
               180                      185                      190

Lys  Cys  Arg  Phe  Pro  Val  Val  Glu  Asn  Gly  Lys  Gln  Ile  Ser  Gly  Phe
          195                      200                      205

Gly  Lys  Lys  Phe  Tyr  Tyr  Lys  Ala  Thr  Val  Met  Phe  Glu  Cys  Asp  Lys
     210                      215                      220

Gly  Phe  Tyr  Leu  Asp  Gly  Ser  Asp  Thr  Ile  Val  Cys  Asp  Ser  Asn  Ser
225                           230                 235                           240

Thr  Trp  Asp  Pro  Pro  Val  Pro  Lys  Cys  Leu  Lys  Val  Ser  Thr
                    245                      250
```

(2) INFORMATION FOR SEQ ID NO:14:

(i) SEQUENCE CHARACTERISTICS:
        (A) LENGTH: 324 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

```
Asp  Cys  Gly  Leu  Pro  Pro  Asp  Val  Pro  Asn  Ala  Gln  Pro  Ala  Leu  Glu
1                    5                  10                      15

Gly  Arg  Thr  Ser  Phe  Pro  Glu  Asp  Thr  Val  Ile  Thr  Tyr  Lys  Cys  Glu
               20                  25                      30

Glu  Ser  Phe  Val  Lys  Ile  Pro  Gly  Glu  Lys  Asp  Ser  Val  Thr  Cys  Leu
          35                       40                      45

Lys  Gly  Met  Gln  Trp  Ser  Asp  Ile  Glu  Glu  Phe  Cys  Asn  Arg  Ser  Cys
     50                       55                  60

Glu  Val  Pro  Thr  Arg  Leu  Asn  Ser  Ala  Ser  Leu  Lys  Gln  Pro  Tyr  Ile
65                       70                       75                       80

Thr  Gln  Asn  Tyr  Phe  Pro  Val  Gly  Thr  Val  Val  Glu  Tyr  Glu  Cys  Arg
                    85                  90                       95

Pro  Gly  Tyr  Arg  Arg  Glu  Pro  Ser  Leu  Ser  Pro  Lys  Leu  Thr  Cys  Leu
               100                      105                      110

Gln  Asn  Leu  Lys  Trp  Ser  Thr  Ala  Val  Glu  Phe  Cys  Lys  Lys  Lys  Ser
               115                      120                      125

Cys  Pro  Asn  Pro  Gly  Glu  Ile  Arg  Asn  Gly  Gln  Ile  Asp  Val  Pro  Gly
     130                      135                      140

Gly  Ile  Leu  Phe  Gly  Ala  Thr  Ile  Ser  Phe  Ser  Cys  Asn  Thr  Gly  Tyr
145                           150                 155                           160

Lys  Leu  Phe  Gly  Ser  Thr  Ser  Ser  Phe  Cys  Leu  Ile  Ser  Gly  Ser  Ser
```

|  |  |  |  |  | 165 |  |  |  |  | 170 |  |  |  |  | 175 |  |
|---|---|---|---|---|---|---|---|---|---|---|---|---|---|---|---|---|

Val Gln Trp Ser Asp Pro Leu Pro Glu Cys Arg Glu Ile Tyr Cys Pro
                180                185                190

Ala Pro Pro Gln Ile Asp Asn Gly Ile Ile Gln Gly Glu Arg Asp His
        195                200                205

Tyr Gly Tyr Arg Gln Ser Val Thr Tyr Ala Cys Asn Lys Gly Phe Thr
    210                215                220

Met Ile Gly Glu His Ser Ile Tyr Cys Thr Val Asn Asn Asp Glu Gly
225                230                235                240

Glu Trp Ser Gly Pro Pro Glu Cys Arg Gly Lys Ser Leu Thr Ser
                245                250                255

Lys Val Pro Pro Thr Val Gln Lys Pro Thr Thr Val Asn Val Pro Thr
            260                265                270

Thr Glu Val Ser Pro Thr Ser Gln Lys Thr Thr Thr Lys Thr Thr Thr
        275                280                285

Pro Asn Ala Gln Ala Thr Arg Ser Thr Pro Val Ser Arg Thr Thr Lys
    290                295                300

His Phe His Glu Thr Thr Pro Asn Lys Gly Ser Gly Thr Thr Ser Gly
305                310                315                320

Thr Thr Arg Leu (2) INFORMATION FOR SEQ ID NO:15:

(i) SEQUENCE CHARACTERISTICS:
  (A) LENGTH: 879 base pairs
  (B) TYPE: nucleic acid
  (C) STRANDEDNESS: double
  (D) TOPOLOGY: linear (ii) MOLECULE TYPE: DNA (xi) SEQUENCE DESCRIPTION: SEQ ID NO:15:

```
TGTGAGGAGC CACCAACATT TGAAGCTATG GAGCTCATTG GTAAACCAAA ACCCTACTAT      60
GAGATTGGTG AACGAGTAGA TTATAAGTGT AAAAAAGGAT ACTTCTATAT ACCTCCTCTT     120
GCCACCCATA CTATTTGTGA TCGGAATCAT ACATGGCTAC CTGTCTCAGA TGACGCCTGT     180
TATAGAGAAA CATGTCCATA TACGGGATCC TTTAAATG GCCAAGCAGT CCCTGCAAAT      240
GGGACTTACG AGTTTGGTTA TCAGATGCAC TTTATTTGTA ATGAGGGTTA TTACTTAATT     300
GGTGAAGAAA TTCTATATTG TGAACTTAAA GGATCAGTAG CAATTTGGAG CGGTAAGCCC     360
CCAATATGTG AAAAGGTTTT GTGTACACCA CCTCCAAAAA TAAAAAATGG AAAACACACC     420
TTTAGTGAAG TAGAAGTATT TGAGTATCTT GATGCAGTAA CTTATAGTTG TGATCCTGCA     480
CCTGGACCAG ATCCATTTTC ACTTATTGGA GAGAGCACGA TTTATTGTGG TGACAATTCA     540
GTGTGGAGTC GTGCTGCTCC AGAGTGTAAA GTGGTCAAAT GTCGATTTCC AGTAGTCGAA     600
AATGGAAAAC AGATATCAGG ATTTGGAAAA AAATTTTACT ACAAAGCAAC AGTTATGTTT     660
GAATGCGATA AGGGTTTTTA CCTCGATGGC AGCGACACAA TTGTCTGTGA CAGTAACAGT     720
ACTTGGGATC CCCCAGTTCC AAAGTGTCTT AAAGTGTCGA CTTCTTCCAC TACAAAATCT     780
CCAGCGTCCA GTGCCTCAGG TCCTAGGCCT ACTTACAAGC CTCCAGTCTC AAATTATCCA     840
GGATATCCTA AACCTGAGGA AGGAATACTT GACAGTTTG                            879
```

(2) INFORMATION FOR SEQ ID NO:16:

(i) SEQUENCE CHARACTERISTICS:
  (A) LENGTH: 293 amino acids
  (B) TYPE: amino acid ( C ) STRANDEDNESS: Not Relevant
( D ) TOPOLOGY: linear ( i i ) MOLECULE TYPE: protein ( x i ) SEQUENCE DESCRIPTION: SEQ ID NO:16:

| Cys | Glu | Glu | Pro | Pro | Thr | Phe | Glu | Ala | Met | Glu | Leu | Ile | Gly | Lys | Pro |
|---|---|---|---|---|---|---|---|---|---|---|---|---|---|---|---|
| 1 | | | | 5 | | | | | 10 | | | | | 15 | |
| Lys | Pro | Tyr | Tyr | Glu | Ile | Gly | Glu | Arg | Val | Asp | Tyr | Lys | Cys | Lys | Lys |
| | | | 20 | | | | | 25 | | | | | 30 | | |
| Gly | Tyr | Phe | Tyr | Ile | Pro | Pro | Leu | Ala | Thr | His | Thr | Ile | Cys | Asp | Arg |
| | | 35 | | | | | 40 | | | | | 45 | | | |
| Asn | His | Thr | Trp | Leu | Pro | Val | Ser | Asp | Asp | Ala | Cys | Tyr | Arg | Glu | Thr |
| | 50 | | | | | 55 | | | | | 60 | | | | |
| Cys | Pro | Tyr | Ile | Arg | Asp | Pro | Leu | Asn | Gly | Gln | Ala | Val | Pro | Ala | Asn |
| 65 | | | | | 70 | | | | | 75 | | | | | 80 |
| Gly | Thr | Tyr | Glu | Phe | Gly | Tyr | Gln | Met | His | Phe | Ile | Cys | Asn | Glu | Gly |
| | | | | 85 | | | | | 90 | | | | | | 95 |
| Tyr | Tyr | Leu | Ile | Gly | Glu | Glu | Ile | Leu | Tyr | Cys | Glu | Leu | Lys | Gly | Ser |
| | | | | 100 | | | | | 105 | | | | | 110 | |
| Val | Ala | Ile | Trp | Ser | Gly | Lys | Pro | Pro | Ile | Cys | Glu | Lys | Val | Leu | Cys |
| | | | 115 | | | | | 120 | | | | | 125 | | |
| Thr | Pro | Pro | Pro | Lys | Ile | Lys | Asn | Gly | Lys | His | Thr | Phe | Ser | Glu | Val |
| | 130 | | | | | 135 | | | | | 140 | | | | |
| Glu | Val | Phe | Glu | Tyr | Leu | Asp | Ala | Val | Thr | Tyr | Ser | Cys | Asp | Pro | Ala |
| 145 | | | | | 150 | | | | | 155 | | | | | 160 |
| Pro | Gly | Pro | Asp | Pro | Phe | Ser | Leu | Ile | Gly | Glu | Ser | Thr | Ile | Tyr | Cys |
| | | | | 165 | | | | | 170 | | | | | 175 | |
| Gly | Asp | Asn | Ser | Val | Trp | Ser | Arg | Ala | Ala | Pro | Glu | Cys | Lys | Val | Val |
| | | | 180 | | | | | 185 | | | | | 190 | | |
| Lys | Cys | Arg | Phe | Pro | Val | Val | Glu | Asn | Gly | Lys | Gln | Ile | Ser | Gly | Phe |
| | | 195 | | | | | 200 | | | | | 205 | | | |
| Gly | Lys | Lys | Phe | Tyr | Tyr | Lys | Ala | Thr | Val | Met | Phe | Glu | Cys | Asp | Lys |
| | 210 | | | | | 215 | | | | | 220 | | | | |
| Gly | Phe | Tyr | Leu | Asp | Gly | Ser | Asp | Thr | Ile | Val | Cys | Asp | Ser | Asn | Ser |
| 225 | | | | | 230 | | | | | 235 | | | | | 240 |
| Thr | Trp | Asp | Pro | Pro | Val | Pro | Lys | Cys | Leu | Lys | Val | Ser | Thr | Ser | Ser |
| | | | | 245 | | | | | 250 | | | | | 255 | |
| Thr | Thr | Lys | Ser | Pro | Ala | Ser | Ser | Ala | Ser | Gly | Pro | Arg | Pro | Thr | Tyr |
| | | | 260 | | | | | 265 | | | | | 270 | | |
| Lys | Pro | Pro | Val | Ser | Asn | Tyr | Pro | Gly | Tyr | Pro | Lys | Pro | Glu | Glu | Gly |
| | | 275 | | | | | 280 | | | | | 285 | | | |
| Ile | Leu | Asp | Ser | Leu | | | | | | | | | | | |
| | | 290 | | | | | | | | | | | | | |

( 2 ) INFORMATION FOR SEQ ID NO:17:

( i ) SEQUENCE CHARACTERISTICS:
( A ) LENGTH: 507 base pairs
( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:17:

AAGGTTTTGT GTACACCACC TCCAAAAATA AAAAATGGAA AACACACCTT TAGTGAAGTA      60

GAAGTATTTG AGTATCTTGA TGCAGTAACT TATAGTTGTG ATCCTGCACC TGGACCAGAT     120

```
CCATTTTCAC TTATTGGAGA GAGCACGATT TATTGTGGTG ACAATTCAGT GTGGAGTCGT      180

GCTGCTCCAG AGTGTAAAGT GGTCAAATGT CGATTTCCAG TAGTCGAAAA TGGAAAACAG      240

ATATCAGGAT TTGGAAAAAA ATTTTACTAC AAAGCAACAG TTATGTTTGA ATGCGATAAG      300

GGTTTTTACC TCGATGGCAG CGACACAATT GTCTGTGACA GTAACAGTAC TTGGGATCCC      360

CCAGTTCCAA AGTGTCTTAA AGTGTCGACT TCTTCCACTA CAAAATCTCC AGCGTCCAGT      420

GCCTCAGGTC CTAGGCCTAC TTACAAGCCT CCAGTCTCAA ATTATCCAGG ATATCCTAAA      480

CCTGAGGAAG GAATACTTGA CAGTTTG                                          507
```

(2) INFORMATION FOR SEQ ID NO:18:

(i) SEQUENCE CHARACTERISTICS:
        (A) LENGTH: 169 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

```
Lys Val Leu Cys Thr Pro Pro Pro Lys Ile Lys Asn Gly Lys His Thr
 1               5                  10                  15

Phe Ser Glu Val Glu Val Phe Glu Tyr Leu Asp Ala Val Thr Tyr Ser
             20                  25                  30

Cys Asp Pro Ala Pro Gly Pro Asp Pro Phe Ser Leu Ile Gly Glu Ser
         35                  40                  45

Thr Ile Tyr Cys Gly Asp Asn Ser Val Trp Ser Arg Ala Ala Pro Glu
     50                  55                  60

Cys Lys Val Val Lys Cys Arg Phe Pro Val Val Glu Asn Gly Lys Gln
 65                  70                  75                  80

Ile Ser Gly Phe Gly Lys Lys Phe Tyr Tyr Lys Ala Thr Val Met Phe
                 85                  90                  95

Glu Cys Asp Lys Gly Phe Tyr Leu Asp Gly Ser Asp Thr Ile Val Cys
            100                 105                 110

Asp Ser Asn Ser Thr Trp Asp Pro Pro Val Pro Lys Cys Leu Lys Val
        115                 120                 125

Ser Thr Ser Ser Thr Thr Lys Ser Pro Ala Ser Ser Ala Ser Gly Pro
    130                 135                 140

Arg Pro Thr Tyr Lys Pro Pro Val Ser Asn Tyr Pro Gly Tyr Pro Lys
145                 150                 155                 160

Pro Glu Glu Gly Ile Leu Asp Ser Leu
                165
```

(2) INFORMATION FOR SEQ ID NO:19:

(i) SEQUENCE CHARACTERISTICS:
        (A) LENGTH: 860 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

```
CCATGACCGT CGCGCGGCCG AGCGTGCCCG CGGCGCTGCC CCTCCTCGGG GAGCTGCCCC       60

GGCTGCTGCT GCTGGTGCTG TTGTGCCTGC CGGCCGTGTG GGGTGACTGT GGCCTTCCCC      120

CAGATGTACC TAATGCCCAG CCAGCTTTGG AAGGCCGTAC AAGTTTTCCC GAGGATACTG      180
```

-continued

| | | | | | | |
|---|---|---|---|---|---|---|
| TAATAACGTA | CAAATGTGAA | GAAAGCTTTG | TGAAAATTCC | TGGCGAGAAG | GACTCAGTGA | 240 |
| CCTGCCTTAA | GGGCATGCAA | TGGTCAGATA | TTGAAGAGTT | CTGCAATCGT | AGCTGCGAGG | 300 |
| TGCCAACAAG | GCTAAATTCT | GCATCCCTCA | AACAGCCTTA | TATCACTCAG | AATTATTTTC | 360 |
| CAGTCGGTAC | TGTTGTGGAA | TATGAGTGCC | GTCCAGGTTA | CAGAAGAGAA | CCTTCTCTAT | 420 |
| CACCAAAACT | AACTTGCCTT | CAGAATTTAA | AATGGTCCAC | AGCAGTCGAA | TTTTGTAAAA | 480 |
| AGAAATCATG | CCCTAATCCG | GGAGAAATAC | GAAATGGTCA | GATTGATGTA | CCAGGTGGCA | 540 |
| TATTATTTGG | TGCAACCATC | TCCTTCTCAT | GTAACACAGG | GTACAAATTA | TTTGGCTCGA | 600 |
| CTTCTAGTTT | TTGTCTTATT | TCAGGCAGCT | CTGTCCAGTG | GAGTGACCCG | TTGCCAGAGT | 660 |
| GCAGAGAAAT | TTATTGTCCA | GCACCACCAC | AAATTGACAA | TGGAATAATT | CAAGGGGAAC | 720 |
| GTGACCATTA | TGGATATAGA | CAGTCTGTAA | CGTATGCATG | TAATAAAGGA | TTCACCATGA | 780 |
| TTGGAGAGCA | CTCTATTTAT | TGTACTGTGA | ATAATGATGA | AGGAGAGTGG | AGTGGCCCAC | 840 |
| CACCTGAATG | CAGAGGAAAA | | | | | 860 |